(12) United States Patent
Ito et al.

(10) Patent No.: US 7,829,586 B2
(45) Date of Patent: Nov. 9, 2010

(54) ARYL-SUBSTITUTED NITROGEN-CONTAINING HETEROCYCLIC COMPOUNDS

(75) Inventors: Hirokatsu Ito, Tsukuba (JP); Kensuke Kobayashi, Ishioka (JP); Hisashi Ohta, Tsukuba (JP); Osamu Okamoto, Ushiku (JP); Satoshi Ozaki, Ushiku (JP); Tomohiro Tsujita, Kagawa (JP)

(73) Assignee: Banyu Pharmaceutical Co., Ltd., Kudankita, Chiyoda-ku, Tokyo (JP)

( * ) Notice: Subject to any disclaimer, the term of this patent is extended or adjusted under 35 U.S.C. 154(b) by 0 days.

(21) Appl. No.: 11/992,817

(22) PCT Filed: Sep. 28, 2006

(86) PCT No.: PCT/JP2006/319912

§ 371 (c)(1),
(2), (4) Date: Feb. 11, 2009

(87) PCT Pub. No.: WO2007/037513

PCT Pub. Date: Apr. 5, 2007

(65) Prior Publication Data

US 2009/0275617 A1 Nov. 5, 2009

(30) Foreign Application Priority Data

Sep. 30, 2005 (JP) .............................. 2005-288545

(51) Int. Cl.
| | |
|---|---|
| *A61K 31/4439* | (2006.01) |
| *A61K 31/415* | (2006.01) |
| *A61K 31/4184* | (2006.01) |
| *C07D 401/02* | (2006.01) |
| *C07D 235/02* | (2006.01) |
| *C07D 231/10* | (2006.01) |

(52) U.S. Cl. ...................... 514/341; 514/396; 514/406; 546/275.4; 548/304.4; 548/373.1

(58) Field of Classification Search ................. 514/341, 514/396, 406; 546/275.4; 548/304.4, 373.1
See application file for complete search history.

(56) References Cited

U.S. PATENT DOCUMENTS 5,624,941 A 4/1997 Barth et al.
6,525,059 B1 2/2003 Anantanarayan et al.
6,960,601 B2 11/2005 Smith
7,125,877 B2 10/2006 Kobayashi et al.
2004/0063691 A1 4/2004 Smith et al.

FOREIGN PATENT DOCUMENTS

| JP | 2002/284779 A | 10/2002 |
|---|---|---|
| WO | WO/006545 | 2/2000 |
| WO | WO/0139775 | 6/2001 |

OTHER PUBLICATIONS

K. Kobayashi et al., "Discovery of Novel Arylpyrazole Series as Potent and Selective Opioid Receptor-Like (ORL 1) Antagonists", vol. 19, pp. 3627-3631, Biorganic & Medicinal Chemistry Letters, 2009.
K. Kobayashi et al., "Identification of MK-1925: A Selective, Orally Active and Brain-Penetrable Opioid Receptor-Like 1 (ORL 1) Antagonist", vol. 19, pp. 4729-4732, Biorganic & Medicinal Chemistry Letters, 2009.

*Primary Examiner*—Kamal A Saeed
*Assistant Examiner*—Samantha L Shterengarts
(74) *Attorney, Agent, or Firm*—J. Eric Thies; Gerard M. Devlin

(57) ABSTRACT

Disclosed is an aryl-substituted nitrogen-containing heterocyclic compound represented by the formula (I) below or a pharmaceutically acceptable salt thereof. This compound serves as nociceptin receptor antagonist and is useful as a pharmaceutical agent for treating diseases associated with a nociceptin receptor. (I)

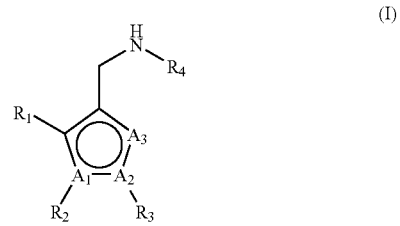

[in the formula, $A_1$, $A_2$ and $A_3$ independently represent a carbon atom or a nitrogen atom, and one or two of $A_1$, $A_2$ and $A_3$ represent a carbon atom; $R^1$ represents a lower alkyl group or the like; $R^2$ represents a phenyl group which may be substituted with a halogen atom or the like; $R^3$ represents a hydrogen atom, a lower alkyl group or the like; and $R^4$ represents a lower alkyl group or the like.]

18 Claims, No Drawings

ARYL-SUBSTITUTED NITROGEN-CONTAINING HETEROCYCLIC COMPOUNDS

CROSS REFERENCE TO RELATED APPLICATIONS

This application is a U.S. National Phase application under 35 U.S.C. §371 of PCT Application No. PCT/JP2006/319912, filed Sep. 28, 2006, which claims priority under 35 U.S.C. §119 from JP Application No. JP2005-288545, filed Sep. 30, 2005.

TECHNICAL FIELD

The present invention relates to a substance having an effect of inhibiting nociceptin from binding to a nociceptin receptor ORL1 (opioid receptor-like-1 receptor). The compound having an effect of inhibiting nociceptin from binding to a nociceptin receptor ORL1 is useful as an analgesic against diseases accompanied with pains such as cancerous pain, postoperative pain, migraine, gout, chronic rheumatism, chronic pain and neuralgia; a reliever against tolerance to narcotic analgesic such as morphine; a reliever against dependence on or addiction to narcotic analgesic such as morphine; an analgesic enhancer; an antiobesitic or appetite suppressor; a treating or prophylactic agent for learning and memory impairment or dementia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an anti-depressant or treating agent for affective disorder; a treating or prophylactic agent for diabetes insipidus; a treating or prophylactic agent for polyuria; a remedy for hypotension et al.

BACKGROUND ART

Nociceptin (the same substance as orphanin FQ) is a peptide comprising 17 amino acid units having a similar structure to that of opioid peptide. Nociceptin has an augmenting activity on reaction against nociceptive stimulation, an appetite stimulating activity, an activity for reducing a space learning ability, an antagonism against an analgesic action of classic opiate agonists, a dopamine release inhibitory action, a water diuresis action, a vasodilative action and a systemic blood pressure-lowering action, and it is considered to take part in intracerebral controlling of pain, appetite and memory learning through the nociceptin receptor ORL1 [see Nature, Vol. 377, 532 (1995); Society for Neuroscience, Vol. 22, 455 (1996); NeuroReport, Vol. 8, 423 (1997); Eur. J. Neuroscience, Vol. 9, 194 (1997); Neuroscience, Vol. 75, 1 (1996); ibid., 333 (1996); Life Science, Vol. 60, PL15 (1997); ibid., PL141 (1997); Proceedings for National Academy of Sciences, Vol. 94, 14858 (1997)].

Further, it is known that morphine tolerance is reduced or memory and learning ability is improved in knockout mice in which expression of nociceptin receptor ORL1 is inhibited [see Neuroscience Letters, Vol. 237, 136 (1997); Nature, Vol. 394, 577 (1998)].

It has also been reported that nociceptin itself induces symptoms resembling withdrawal symptoms observed in morphine withdrawal, and that a non-peptide nociceptin receptor antagonist improves morphine tolerance, dependence and symptoms resembling withdrawal symptoms [see Psychopharmacology, Vol. 151, 344-350 (2000); Journal of Neuroscience, Vol. 20, 7640 (2000)].

On the other hand, nociceptin protein precursor-defective mice are reported to show behaviors resembling anxiety and changes in stress response [see Proceedings for National Academy of Sciences, Vol. 96, 10444 (1999)].

Hence the substances which specifically inhibit binding of nociceptin to the nociceptin receptor ORL1 are useful as an analgesic against diseases accompanied with pains such as cancerous pain, postoperative pain, migraine, gout, chronic rheumatism, chronic pain and neuralgia; a reliever against tolerance to narcotic analgesic such as morphine; a reliever against dependence on or addiction to narcotic analgesic such as morphine; an analgesic enhancer; an antiobesitic or appetite suppressor; a treating or prophylactic agent for learning and memory impairment or dementia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as typically Parkinsonism and chorea; an anti-depressant or treating agent for affective disorder; a treating or prophylactic agent for diabetes insipidus; a treating or prophylactic agent for polyuria; a remedy for hypotension, etc.

JP-A 6-73014 discloses pyrazole compounds similar to the compounds of the invention as a cannabinoid receptor ligand. WO2003/40107 discloses imidazole compounds similar to the compounds of the invention. However, the compounds concretely disclosed in these descriptions have an alkyl phenyl as the part of $R^3$ in a formula (I) in the present invention; but in the invention, $R^3$ should not be a phenyl group; and therefore, the compounds differ from those in the present invention.

Patent Reference 1: JP-A 6-73014
Patent Reference 2: WO2003/40107

DISCLOSURE OF THE INVENTION

The present inventors have assiduously studied aryl-substituted nitrogen-containing heterocyclic compounds as those having an effect of inhibiting the binding of nociceptin to a nociceptin receptor ORL1, and, as a result, have found that compounds having a specific substituent are antagonistic to the binding of nociceptin to a nociceptin receptor ORL1, and, on the basis of those findings, have completed the present invention.

Specifically, the invention provides an aryl-substituted nitrogen-containing heterocyclic compound of a formula (1) or a pharmaceutically-acceptable salt thereof:

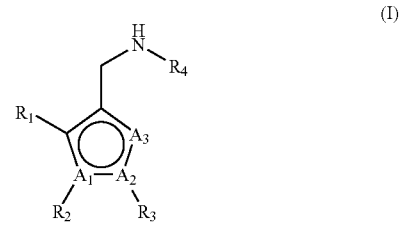

[wherein,
$A_1$, $A_2$ and $A_3$ are same or different, each representing a carbon atom or a nitrogen atom; but at least one or two of $A_1$, $A_2$ and $A_3$ are carbon atoms, and the other is a nitrogen atom;

$R^1$ represents a halogen atom, a lower alkyl group optionally substituted with a lower alkoxy group, or a phenyl group substituted with a halogen atom;

$R^2$ represents a phenyl group optionally substituted with a halogen atom and/or a lower alkyl group; a pyridinyl group optionally substituted with a halogen atom and/or a lower alkyl group; or a thiazolyl group optionally substituted with a halogen atom and/or a lower alkyl group;

$R^3$ represents a hydrogen atom; a lower alkyl group optionally substituted with a hydroxyl group, a halogen atom, a lower alkoxy group or a cyano group; a lower cycloalkyl group optionally substituted with a hydroxyl group or a halogen atom;

$R^4$ represents a lower alkyl group; a lower cycloalkyl group optionally substituted with a halogen atom, a hydroxyl group or a lower alkoxy group; a lower cycloalkyl-lower alkyl group optionally substituted with a halogen atom, a hydroxyl group or a lower alkoxy group; or a tetrahydro-2H-pyran-4-yl group].

Further, the invention provides, (2) A nociceptin receptor antagonist containing the compound of (1) or the pharmaceutically-acceptable salt thereof as the active ingredient;

(3) A pharmaceutical composition comprising pharmaceutically-acceptable additives and an effective amount of the compound of (1) or the pharmaceutically-acceptable salt thereof;

(4) An analgesic; a reliever against tolerance to narcotic analgesic such as morphine; a reliever against dependence on or addiction to narcotic analgesic such as morphine; an analgesic enhancer; an antiobesitic or appetite suppressor; a treating or prophylactic agent for learning and memory impairment or dementia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an anti-depressant or treating agent for affective disorder; a treating or prophylactic agent for diabetes insipidus; a treating or prophylactic agent for polyuria; a remedy for hypotension, which contains the compound of (1) or the pharmaceutically-acceptable salt thereof as the active ingredient.

The invention is described further in detail hereinunder.

In this description,

"Halogen atom" includes a fluorine atom, a chlorine atom, a bromine atom and an iodine atom.

"Lower alkyl group" includes a linear alkyl group having from 1 to 6 carbon atoms, and a branched alkyl group having from 3 to 6 carbon atoms. Concretely, for example, it includes a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-amyl group, a 1-methylbutyl group, a 2-methylbutyl group, a 1,2-dimethylpropyl group, a 1-ethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, a 1-ethyl-1-methylpropyl group et al.

"Lower cycloalkyl group" includes a cycloalkyl group having from 3 to 6 carbon atoms. Concretely, for example, it includes a cyclopropyl group, a cyclobutyl group, a cyclopentyl group, and a cyclohexyl group.

"Lower alkyloxy group" includes a group of an oxygen atom to which a lower alkyl group bonds. Concretely, it includes a methoxy group, an ethoxy group, a n-propyloxy group, an isopropyloxy group, a n-butoxy group, an isobutoxy group, a tert-butoxy group, a n-pentyloxy group et al.

"Lower cycloalkyl-lower alkyl group" means a group of a lower alkyl group in which one hydrogen atom is substituted with a lower cycloalkyl group, and concretely, it includes a cyclopropylmethyl group, a 2-cyclopropylethyl group, a cyclobutylmethyl group, a 2-cyclobutylethyl group, a cyclopentylmethyl group, a 2-cyclopentylethyl group, a cyclohexylmethyl group, a 2-cyclohexylethyl group et al.

"Pharmaceutically-acceptable salts" of compounds of the formula (I) include ordinary salts that are acceptable as drugs, for example, acid-addition salts at the nitrogen-containing hetero ring of the compounds of the formula (I).

The acid-addition salts includes inorganic acid salts such as hydrochlorides, sulfates, acetates, hydrobromides, phosphates et al; organic acid salts such as maleates, fumarates, tartrates, citrates et al; and sulfonates such as methanesulfonates et al.

The compounds of the invention are described in detail hereinunder with reference to their examples.

In the formula (I), $A_1$, $A_2$ and $A_3$ are same or different, each representing a carbon atom or a nitrogen atom; but at least one or two of $A_1$, $A_2$ and $A_3$ are carbon atoms, and the other is a nitrogen atom.

Concrete combinations of $A_1$, $A_2$ and $A_3$ include the following:

$A_1$ is a nitrogen atom, and $A_2$ and $A_3$ are carbon atoms, $A_2$ is a nitrogen atom, and $A_1$ and $A_3$ are carbon atoms, $A_3$ is a nitrogen atom, and $A_1$ and $A_2$ are carbon atoms, $A_1$ is a carbon atom, and $A_2$ and $A_3$ are nitrogen atoms, $A_2$ is a carbon atom, and $A_1$ and $A_3$ are nitrogen atoms, $A_3$ is a carbon atom, and $A_1$ and $A_2$ are nitrogen atoms, et al.

Of those, preferred are combinations where two of $A_1$, $A_2$ and $A_3$ are nitrogen atoms; and more preferred are the following:

1) $A_2$ and $A_3$ are nitrogen atoms, and $A_1$ is a carbon atom,

2) $A_1$ and $A_3$ are nitrogen atoms, and $A_2$ is a carbon atom.

$R^1$ represents a halogen atom, a lower alkyl group optionally substituted with a lower alkoxy group, or a phenyl group substituted with a halogen atom;

Concretely, $R^1$ includes a halogen atom such as fluorine, chlorine, bromine et al; a lower alkyl group optionally substituted with a lower alkoxy group, such as a methyl group, an ethyl group, a n-propyl group, an isopropyl group, a n-butyl group, a t-butyl group, a methoxymethyl group, a methoxyethyl group, an ethoxymethyl group, an ethoxyethyl group et al; a phenyl group substituted with a halogen atom, such as an o-fluorophenyl group, an o, p-difluorophenyl group, an o-chlorophenyl group, an o, p-dichlorophenyl group et al; more preferably a methyl group, an ethyl group, an isopropyl group, a methoxyethyl group et al.

$R^2$ represents a phenyl group optionally substituted with a halogen atom and/or a lower alkyl group; a pyridinyl group optionally substituted with a halogen atom and/or a lower alkyl group; or a thiazolyl group optionally substituted with a halogen atom and/or a lower alkyl group.

Concretely, $R^2$ includes a phenyl group, a 3-chlorophenyl group, a 4-chlorophenyl group, a 3-fluorophenyl group, a 4-fluorophenyl group, a 3-methylphenyl group, a 4-methylphenyl group, a 3-ethylphenyl group, a 4-ethylphenyl group, a 3,5-dichlorophenyl group, a 3,4-difluorophenyl group, a 3,5-difluorophenyl group, a 3-chloro-5-fluorophenyl group, a 3,4,5-trifluorophenyl group, a 4-chloro-3,5-difluorophenyl group, a 5-fluoro-3-methylphenyl group, a pyridin-3-yl group, a 2-chloropyridin-5-yl group, a 3-chloropyridin-5-yl group, a 2-methylpyridin-5-yl group, a 3-fluoro-2-methylpyridin-5-yl group, a 6-fluoro-2-methylpyridin-5-yl group, a 3-chloro-2-methylpyridin-5-yl group, a 2-methyl-1,3-thiazol-5-yl group, a 2-chloro-1,3-thiazol-5-yl group, a 2,4-dimethyl-1,3-thiazol-5-yl group et al; preferably a 4-fluorophenyl group, a 3,5-difluorophenyl group, a 3,4,5-trifluorophenyl group, a 4-chloro-3,5-difluorophenyl group, a 3-fluoro-2-methylpyridin-5-yl group, a 2-methylpyridin-5-yl group, a 2-methyl-1,3-thiazol-5-yl group et al.

$R^3$ represents a hydrogen atom; a lower alkyl group optionally substituted with a hydroxyl group, a halogen atom, a lower alkoxy group or a cyano group; a lower cycloalkyl group optionally substituted with a hydroxyl group or a halogen atom.

Concretely, $R^3$ includes, in addition to a hydrogen atom, a lower alkyl group optionally substituted with a hydroxyl group, a halogen atom, a lower alkoxy group or a cyano group, such as a methyl group, an ethyl group, a 2-fluoroethyl group, a 2-cyanoethyl group, a n-propyl group, an isopropyl group, a n-butyl group, an isobutyl group, a tert-butyl group et al; a lower cycloalkyl group optionally substituted with a hydroxyl group or a halogen atom, such as a cyclopropyl group, a cyclobutyl group, a cyclopentyl group et al.

Preferably, $R^3$ includes a hydrogen atom, a methyl group, an ethyl group, a n-propyl group, an isopropyl group, a tert-butyl group, a 2-cyanoethyl group, a cyclopropyl group et al.

$R^4$ represents a lower alkyl group; a lower cycloalkyl group optionally substituted with a halogen atom, a hydroxyl group or a lower alkoxy group; a lower cycloalkyl-lower alkyl group optionally substituted with a halogen atom, a hydroxyl group or a lower alkoxy group; or a tetrahydro-2H-pyran-4-yl group.

Concretely, $R^4$ includes a lower alkyl group such as a methyl group, an ethyl group, a n-propyl group, an isopropyl group, a n-butyl group, an isobutyl group, a tert-butyl group et al; a lower cycloalkyl group optionally substituted with a halogen atom, a hydroxyl group or a lower alkoxy group, such as a cyclopropyl group, a cyclobutyl group, a cyclopentyl group, a 3-hydroxycyclopentyl group, a 2-fluorocyclopentyl group, a 3-fluorocyclopentyl group, a cyclohexyl group, a 4-methoxycyclohexyl group, a 4-fluorocyclohexyl group et al; a tetrahydro-2H-pyran-4-yl group; more preferably, a 3-fluorocyclopentyl group, a 3-hydroxycyclopentyl group, a 4-methoxycyclohexyl group, a 4-fluorocyclohexyl group, a tetrahydro-2H-pyran-4-yl group et al.

Preferred examples of the compounds of a formula (I) are:

(a) a compound of a formula (I-a) or a pharmaceutically-acceptable salt thereof:

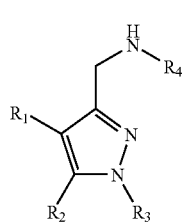

(I-a)

[wherein $R^1$, $R^2$, $R^3$ and $R^4$ have the same meanings as above], (b) a compound of a formula (I-b) or a pharmaceutically-acceptable salt thereof:

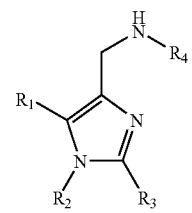

(I-b)

[wherein $R^1$, $R^2$, $R^3$ and $R^4$ have the same meanings as above], (c) a compound of a formula (I-c) or a pharmaceutically-acceptable salt thereof:

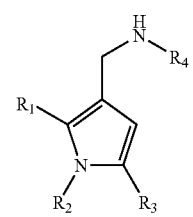

(I-c)

[wherein $R^1$, $R^2$, $R^3$ and $R^4$ have the same meanings as above].

The compounds of a formula (I) are preferably the following:

1) 3-[(1S,3R)-3-fluorocyclopentylamino]methyl-5-(5-fluoro-6-methylpyridin-3-yl)-1-isopropyl-4-methyl-1H-pyrazole,
2) 5-(3,5-difluorophenyl-3-[(1S,3R)-3-fluorocyclopentylamino]methyl-4-methyl-1H-pyrazole,
3) 1-(2-cyanoethyl)-5-(3,5-difluorophenyl)-3-[(1S,3R)-3-fluorocyclopentylamino]methyl-4-methyl-1H-pyrazole,
4) 5-(3,5-difluorophenyl)-3-[(1S,3R)-3-fluorocyclopentylamino]methyl-4-methoxymethyl-1-methyl-1H-pyrazole,
5) 1-(3,5-difluorophenyl)-5-ethyl-2-methyl-4-[(1S,3R)-3-fluorocyclopentylamino]methyl-1H-imidazole,
6) 5-(3,5-difluorophenyl)-3-[(1S,3R)-3-fluorocyclopentylamino]methyl-4-methoxymethyl-1H-pyrazole,
7) 5-(3,5-difluorophenyl)-3-[(1S,2R)-2-fluorocyclopentylamino]methyl-4-methoxymethyl-1H-pyrazole,
8) 1-cyclopropyl-5-(3,5-difluorophenyl)-3-[(1S,3R)-3-fluorocyclopentylamino]methyl-4-methyl-1H-pyrazole,
9) 5-(3,5-difluorophenyl)-3-(cyclopentylamino)methyl-4-methoxymethyl-1H-pyrazole,
10) 3-[(1S,3R)-3-fluorocyclopentylamino]methyl-4-methoxymethyl-5-(3,4,5-trifluorophenyl)-1H-pyrazole,
11) 5-(4-chloro-3,5-difluorophenyl)-1-ethyl-3-[(1S,3R)-3-fluorocyclopentylamino]methyl-4-methyl-1H-pyrazole, and
12) 1-(3,5-difluorophenyl)-4-(cis-4-fluorocyclohexylamino)methyl-5-ethyl-2-methyl-1H-imidazole, et al;

more preferably, the following:

a) 3-[(1S,3R)-3-fluorocyclopentylamino]methyl-5-(5-fluoro-6-methylpyridin-3-yl)-1-isopropyl-4-methyl-1H-pyrazole,
b) 5-(3,5-difluorophenyl-3-[(1S,3R)-3-fluorocyclopentylamino]methyl-4-methyl-1H-pyrazole,
c) 1-(2-cyanoethyl)-5-(3,5-difluorophenyl)-3-[(1S,3R)-3-fluorocyclopentylamino]methyl-4-methyl-1H-pyrazole,
d) 1-(3,5-difluorophenyl)-5-ethyl-2-methyl-4-[(1S,3R)-3-fluorocyclopentylamino]methyl-1H-imidazole,
e) 5-(3,5-difluorophenyl)-3-[(1S,3R)-3-fluorocyclopentylamino]methyl-4-methoxymethyl-1H-pyrazole,
f) 1-(3,5-difluorophenyl)-4-(cis-4-fluorocyclohexylamino)methyl-5-ethyl-2-methyl-H-imidazole, et al.

Production Methods for a Compound of a Formula (I)

Production Method 1-1:

A compound of a formula (I) wherein $A_1$ is a carbon atom, $A_2$ and $A_3$ are nitrogen atoms, or that is, a compound of a formula (I-a) can be produced according to the following production method:

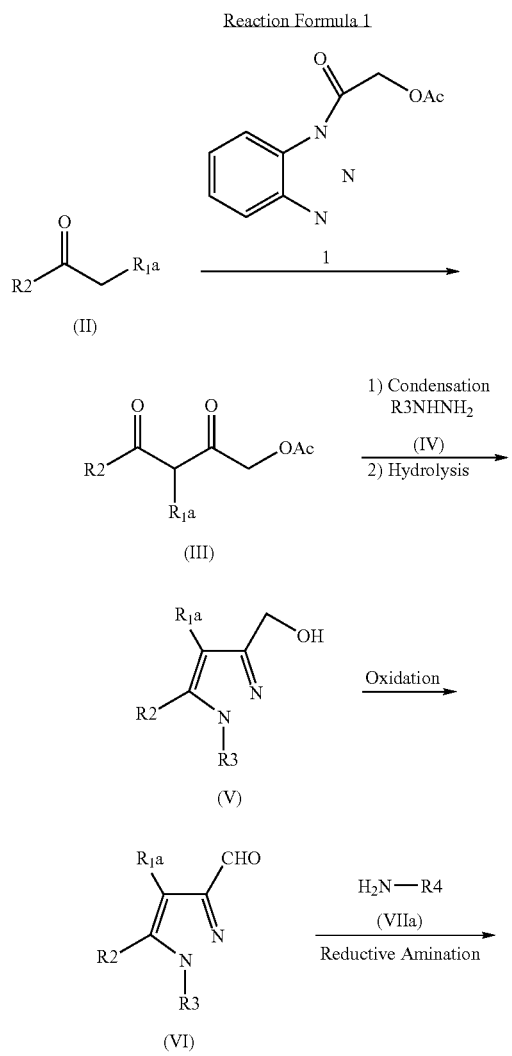

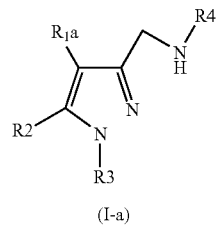

[In the formula, $R^{1a}$ represents a lower alkyl group optionally substituted with a lower alkoxy group, or a phenyl group optionally substituted with a halogen; $R^2$, $R^3$ and $R^4$ are the same as above.]

A compound of a formula (II) is condensed with a compound 1 in an organic solvent in the presence of a base to obtain a compound of a formula (III).

The amount of the compound 1 to be used may be from 1 to 2 mols, preferably from 1 to 1.5 mols relative to 1 mol of the compound of the formula (II).

The base includes lithium hexamethyldisilazide, sodium hexamethyldisilazide, potassium hexamethyldisilazide et al, preferably lithium hexamethyldisilazide.

The amount of the base to be used may be from 1 to 3 mols, preferably from 1 to 2 mols relative to 1 mol of the compound of the formula (II).

The organic solvent includes ethers such as diethyl ether, tetrahydrofuran (hereinafter referred to as "THF") and 1,4-dioxane (hereinafter referred to as dioxane) et al; N,N-dimethylformamide (hereinafter referred to as "DMF"), dimethyl sulfoxide (hereinafter referred to as "DMSO") et al.

The reaction temperature may be from −78 to 20° C., preferably from −78 to 0° C., and in general, the reaction is completed in 1 to 2 hours.

In a preferred embodiment, a compound of a formula (II) is reacted with a base at −78° C., and then a compound 1 is successively added to the reaction mixture for condensation to obtain a compound of a formula (III).

The reaction liquid containing the compound of the formula (III) produced according to the above method contains remaining reagents and by-products, and therefore, the compound of the formula (III) can be isolated through extraction or purification according to a conventional known method. (The same shall apply to the production methods mentioned hereunder.)

Next, the compound of the formula (III) is condensed with a compound of a formula (IV) in an organic solvent or in a hydrochloric acidic organic solvent, and the acetyl group of the obtained compound is hydrolyzed to obtain a compound of a formula (V).

The amount of the compound of the formula (IV) to be used may be from 1 to 4 mols, preferably from 1 to 2 mols relative to 1 mol of the compound of the formula (III).

The organic solvent includes alcohol solvents such as methanol, ethanol, n-propanol, isopropanol et al; ethers such as diethyl ether, THF, dioxane et al; DMF, DMSO et al.

The hydrochloric acidic organic solvent includes, for example, 4 M-hydrogen chloride/dioxane, 4 M-hydrogen chloride/methanol.

The reaction temperature may be from 0 to 150° C., preferably from 20 to 90° C., and in general, the reaction is completed in 1 to 24 hours.

The acetyl group can be hydrolyzed in a conventional known method.

Next, the compound of the formula (V) is oxidized in an organic solvent to obtain a compound of a formula (VI).

The oxidizing agent includes manganese dioxide, Dess-Martin periodinane (hereinafter referred to as "DMP").

The amount of the oxidizing agent to be used may be as follows:

1) When DMP is used, its amount may be from 1 to 4 mols, preferably from 1 to 2 mols relative to 1 mol of the compound of the formula (V).

2) When manganese dioxide is used, its amount may be from 100 to 600 parts by weight, preferably from 200 to 400 parts by weight relative to 100 parts by weight of the compound of the formula (V).

For any of those oxidizing agents, the organic solvent may be ethers such as diethyl ether, THF, dioxane et al; halogenohydrocarbons such as methylene chloride, chloroform, carbon tetrachloride et al; DMF, DMSO et al.

The reaction temperature may be as follows:

1) When DMP is used, it may be from 0 to 100° C., preferably from 0 to 30° C.; and in general, the reaction is completed in 0.5 to 2 hours.

2) When manganese dioxide is used, it may be from 0 to 50° C., preferably from 10 to 30° C., and in general, the reaction is completed in 1 to 24 hours.

The compound of the formula (VI) is subjected to reductive amination with a compound of a formula (VIIa) in an organic solvent in the presence of a reducing agent to obtain a compound of a formula (I-a).

Regarding the amount to be used of the compound of the formula (VI) and that of the compound of the formula (VIIa), in general, the two may be used each in an equimolar amount, or any one of them may be used in a small excessive molar amount.

The reducing agent includes sodium cyanoborohydride, sodium triacetoxyborohydride, zinc biscyanoborohydride, nickel biscyanoborohydride et al.

The amount of the reducing agent to be used may be from 1 mol to an excessive molar amount, preferably from 1 to 5 mols relative to 1 mol of the compound of the formula (VI).

The organic solvent includes alcohols such as methanol, ethanol, propanol et al; ethers such as diethyl ether, THF, dioxane et al; halogenohydrocarbons such as methylene chloride, chloroform, dichloroethane et al; aromatic hydrocarbons such as benzene, toluene, chlorobenzene, xylene et al; other solvents such as DMF, acetonitrile et al; and their mixed solvents.

The reaction temperature may be generally from –20° C. to 100° C., preferably from 0° C. to room temperature; and the reaction time may be generally from 5 minutes to 7 days, preferably from 1 hour to 6 hours.

The compound of the formula (II) includes, for example, the following:

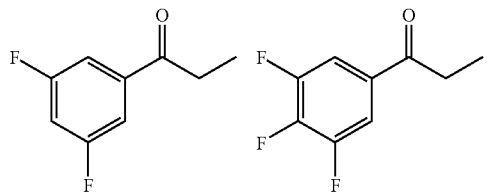

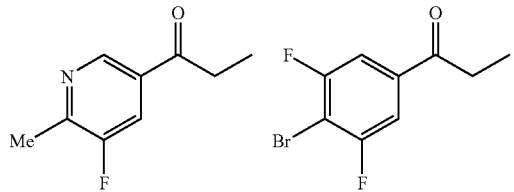

The compound of the formula (IV) includes, for example, hydrazine, methylhydrazine, ethylhydrazine, n-propylhydrazine, isopropylhydrazine, tert-butylhydrazine, cyclopropylhydrazine, 2-cyanoethylhydrazine et al.

The compound of the formula (VIIa) includes the following:

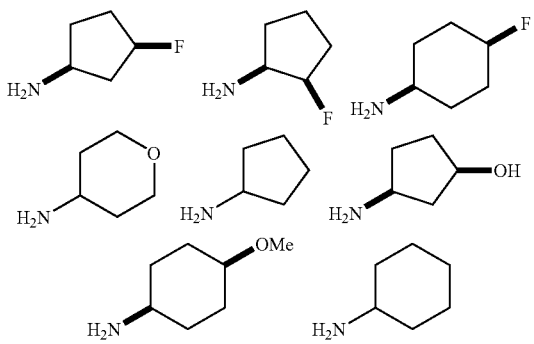

Production Method 1-2:

A compound of the formula (III) can also be produced according to the following method:

Reaction Formula 2

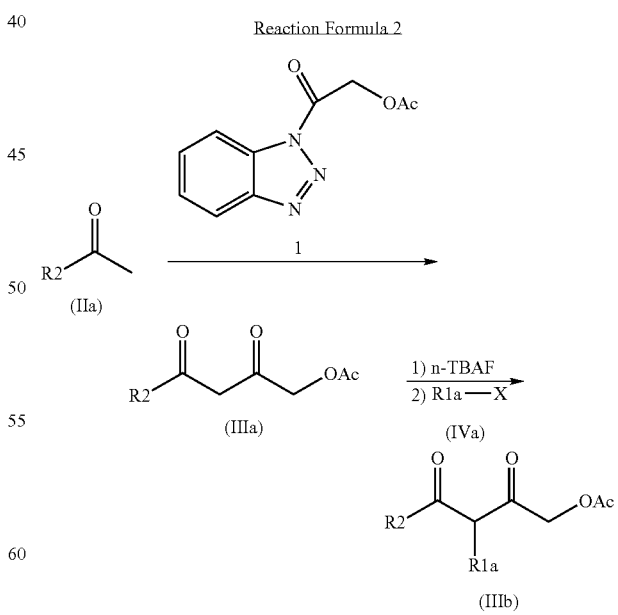

[In the formula, X represents a halogen such as a fluorine atom, a chlorine atom et al; $R^{1a}$, $R^2$ and X are the same as above.]

Specifically, a compound of a formula (IIa) is condensed with a compound 1 in accordance with the production method 1, thereby giving a compound of a formula (IIIa). Next, the compound of the formula (IIIa) is reacted with n-tetrabutylammonium fluoride (n-TBAF) added thereto in an organic solvent at a temperature of from 0 to 30° C. for 1 to 30 minutes, and then a compound of a formula (IVa) is added to the reaction mixture for condensation to obtain a compound of a formula (IIIb) (see J. Chem. Soc., Perkin Trans. I. 1977, 1743-1745).

The amount of n-TBAF to be used may be from 1 to 5 mols, preferably from 1 to 1.5 mols relative to 1 mol of the compound of the formula (IIIa).

The reaction solvent includes ethers such as diethyl ether, THF, dioxane et al.

The amount of the compound (IVa) to be used may be from 1 to 10 mols, preferably from 1 to 5 mols relative to 1 mol of the compound of the formula (IIa).

The reaction temperature may be from 30 to 100° C., preferably from 30 to 80° C.; and in general, the reaction is completed in 1 to 24 hours.

Next, the compound of the formula (IIIb) is reacted in accordance with the production method 1, thereby giving a compound of a formula (I-a).

The compound of the formula (IIa) and the compound of the formula (IVa) include 3,5-difluoroacetophenone, 3,4,5-trifluoroacetophenone, 5-acetyl-2-picoline et al; and in addition to these, also other commercially-available reagents are available, and still others may be prepared according to conventional known methods.

Production Method 1-3:

Production method 1-3 is a method for producing a compound of a formula (I-a) where $R^1$ is halogen, or that is, a compound of a formula (I-a').

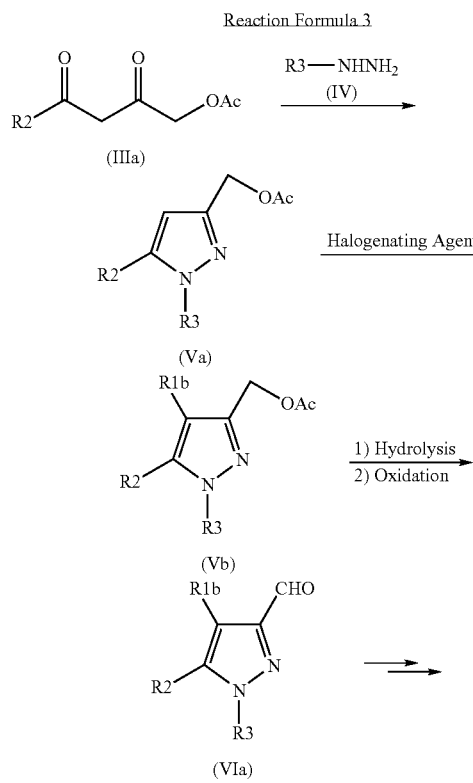

Reaction Formula 3

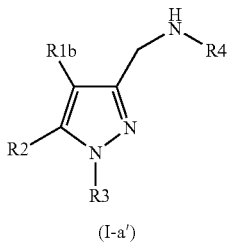

(I-a')

[In the formula, $R^{1b}$ represents a halogen atom; $R^2$, $R^3$ and $R^4$ are the same as above.]

Specifically, a compound of a formula (IIIa) is condensed with a compound of a formula (IV) according to the production method 1-1 to obtain a compound of a formula (Va), and then the compound of the formula (Va) is reacted with a halogenating agent such as N-chlorosuccinimide, N-bromosuccinimide or N-iodosuccinimide et al, to obtain a compound of a formula (Vb). The halogenation can be attained by using a conventional known method.

Next, the compound of the formula (Vb) is hydrolyzed at the acetyl group thereof, and then the obtained alcohol is oxidized according to the production method 1 to obtain a compound of a formula (VIa). Further, the compound of the formula (VIa) is reacted according to the production method 1 to obtain a compound of a formula (I-a').

As the compound of the formula (IIIa), usable are those described in Examples and commercially-available reagents, and in addition, they can be prepared by conventional known methods.

Production Method 1-4:

Production method 1-4 is an alternative method for producing the compound of the formula (I-a).

Reaction Formula 4

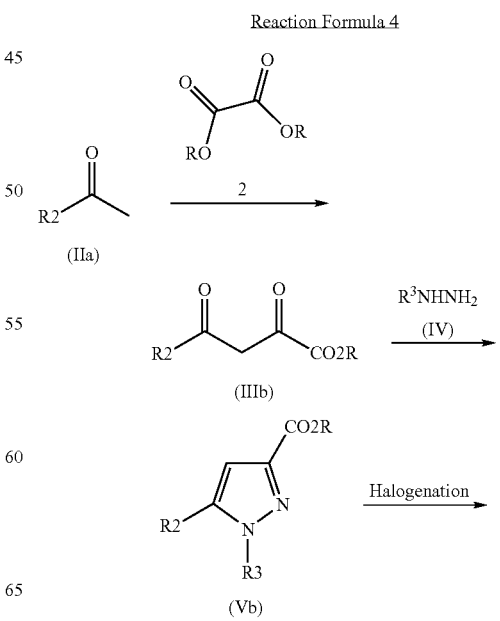

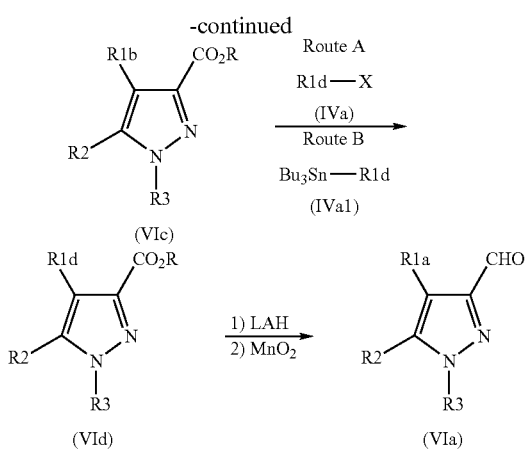

[In the formula, R represents an alkyl group having from 1 to 4 carbon atoms; $R^{1d}$ represents $R^{1a}$, a vinyl group or an isopropenyl group; X, $R^{1b}$, $R^2$ and $R^3$ are the same as above.]

A compound of a formula (IIa) is reacted with a compound 2 according to the production method 1 to obtain a compound of a formula (IIIb). Next, the compound of the formula (IIIb) is reacted according to the production method 1-3 to obtain a compound of a formula (VIc).

With that, the compound of the formula (VIc) is subjected to halogen-metal exchange reaction, and then the obtained product is alkylated with a compound of a formula (IVa) (route A), or the compound of the formula (VIc) is coupled with a compound of a formula (IVa1) using Pd (route B) to obtain a compound of a formula (VId).

Route A:

The halogen-metal exchange reaction with the compound of the formula (VIc) is attained in an organic solvent in the presence of an alkyl metal reagent.

The alkyl metal reagent includes n-butyllithium, sec-butyllithium, tert-butyllithium et al.

The amount of the alkyl organometal may be from 1 to 3 mols, preferably from 1 to 1.5 mols relative to 1 mol of the compound of the formula (VIc).

The organic solvent includes ethers such as diethyl ether, THF, dioxane et al.

The reaction temperature may be from −100° C. to 50° C., preferably from −78° C. to 20° C.; and in general, the reaction is completed in 0.5 to 2 hours.

Next, the reaction mixture is alkylated with a compound of a formula (IVa) added thereto, preferably at −78° C.

The amount of the compound of the formula (IVa) to be used may be from 1 to 3 mols, preferably from 1 to 1.5 mols relative to 1 mol of the compound of the formula (VIc).

The reaction temperature may be from −100° C. to 50° C., preferably from −78° C. to 20° C.; and in general, the reaction is completed in 1 to 2 hours.

Route B:

The coupling reaction of the compound of the formula (VIc) with a compound of a formula (IVa1) is attained in an organic solvent in the presence of a catalytic amount of palladium.

The amount of the compound of the formula (IVa1) to be used may be from 1 to 3 mols, preferably from 1 to 1.5 mols relative to 1 mol of the compound of the formula (VIc).

The reaction temperature may be from 50 to 200° C., preferably from 70 to 150° C.; and in general, the reaction is completed in 1 to 24 hours.

The compound of the formula (VId) obtained in the above is reduced with lithiumaluminium hydride at the ester moiety thereof, then oxidized with manganese dioxide to give a compound of a formula (VIa).

In this, $R^{1d}$, a vinyl group may be converted into an ethyl group, and an isopropenyl group may be converted into an isopropyl group, through hydrogenation.

The compound of the formula (IVa1) includes tributyl(vinyl)tin, tributyl(isopropenyl)tin et al. And commercially-available reagents can be used, or they can be prepared by conventional known methods.

Production Method 1-5:

Using the following compound 3 in place of the compound 2, the same reaction as in the production method 1-4 may be attained to obtain a compound of a formula (IVa).

Reaction Formula 5

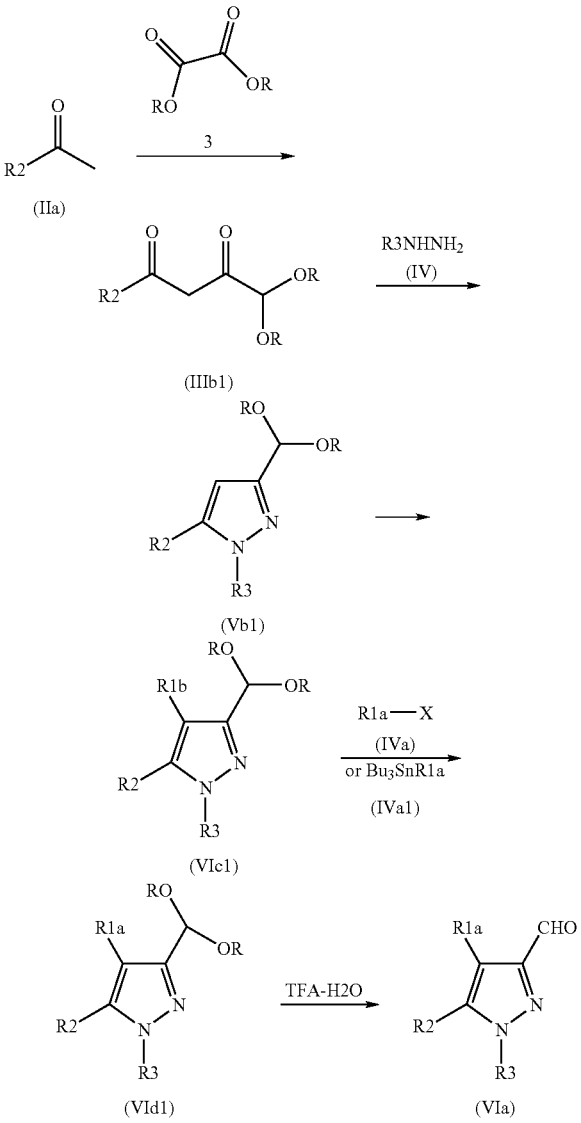

[In the formula, R, $R^{1a}$, $R^{1b}$, $R^2$, $R^3$ and X are the same as above.]

Specifically, a compound of a formula (IIa) is reacted with a compound 3 according to the production method 1-4 successively to obtain a compound of a formula (VId1). With that, the obtained compound of the formula (VId1) is reacted in a mixed solvent of trifluoroacetic acid (hereinafter referred to as "TFA")/water at a temperature of 0 to 100° C. for 1 to 24 hours to give a compound of a formula (VIa).

In case where $R^3$ in the compound of the formula (IV) is a hydrogen atom, the amino group in the compound of the formula (Vb1) may be protected with a trimethylsilylethoxymethyl group (hereinafter referred to as "SEM group"), and then the compounds are condensed, whereupon SEM may be removed in treatment of the compound of the formula (VId1) with TFA.

The introduction and the removal of the protective group may vary depending on the type of the protective group and on the stability of the product compound; but for example, it may be attained according to methods described in literature [see Protective Groups in Organic Synthesis, T. W. Greene, John Wiley & Sons (1981)] or according to methods similar to them. Concretely, for example, it may be attained through solvolysis with acid or base, or that is, according to a method of reaction with from 0.01 mol to a large excessive amount of an acid, preferably trifluoroacetic acid, formic acid, hydrochloric acid et al, or with from an equimolar amount to a large excessive amount of a base, preferably potassium hydroxide, calcium hydroxide et al; or through chemical reduction with a metal hydride complex et al; or through catalytic reduction with a palladium-carbon catalyst, a Raney nickel catalyst et al.

Production Method 2:

A compound of the formula (I) where $A_2$ is a carbon atom, and $A_1$ and $A_3$ are nitrogen atoms, or that is a compound of a formula (I-b) may be produced according to the following production method:

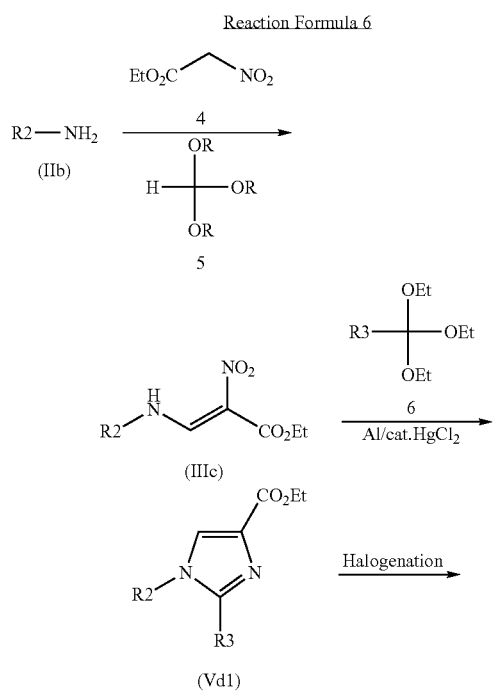

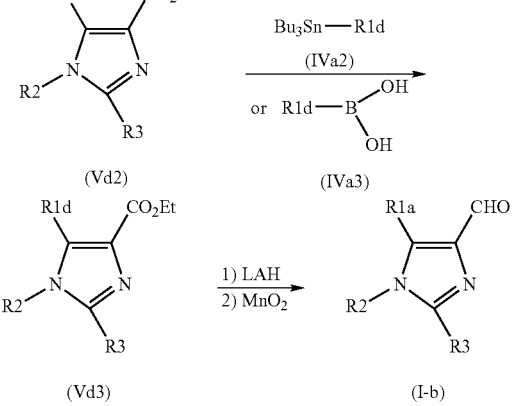

[In the formula, $R^{1d}$, $R^{1a}$, $R^{1b}$, $R^2$, $R^3$ and R are the same as above.]

A compound of a formula (IIb) is condensed with ethyl nitroacetate (compound 4) in acetic acid in the presence of a compound 5 to obtain a compound of a formula (IIIc) [see An. Quim., C, 81, 139 (1985)].

The amount of ethyl nitroacetate to be used may be from 1 to 5 mols, preferably from 1 to 2 mols relative to 1 mol of the compound of the formula (IIb). The amount of the compound 5 to be used may be from 1 to 5 mols relative to 1 mol of the compound of the formula (IIb).

The reaction temperature may be from 80 to 200° C., preferably from 100 to 120° C.; and in general, the reaction is completed in 1 to 4 hours.

Next, the compound of the formula (IIIc) is condensed with a compound 6 in an organic solvent in the presence of aluminium and mercury chloride, to obtain a compound of a formula (Vd1) [see J. Heterocyclic Chem., 24, 1757 (1987)].

The amount of the compound 6 to be used may be from 1 to 10 mols, preferably from 2 to 3 mols relative to 1 mol of the compound of the formula (IIIc).

The amount of mercury chloride to be used may be from 0.01 to 0.2 mols, preferably from 0.01 to 0.05 mols relative to 1 mol of the compound of the formula (IIIc). The amount of aluminium to be used may be from 1 to 10 mols, preferably from 2 to 4 mols relative to 1 mol of the compound of the formula (IIIc).

The reaction temperature may be from 50 to 100° C., preferably from 60 to 80° C.; and in general, the reaction is completed in 1 to 5 hours.

Next, the compound of the formula (Vd1) can be reacted according to the production method 1-4 to obtain a compound of a formula (I-b).

The compound of the formula (IIb) includes 3,5-difluoroaniline, 3,4,5-trifluoroaniline et al; and commercially-available reagents may be used for them, or they may be prepared in conventional known methods.

Further, for the compound of the formula (IVa2) and the compound of the formula (IVa3), those described in Examples or commercially-available reagents may be used, and in addition, they may be prepared according to conventional known methods.

Production Method 3:

A compound of the formula (I), where $A_2$ and $A_3$ are carbon atoms, and $A_1$ is a nitrogen atom, or that is, a compound of a formula (I-c) may be produced according to the following production method:

Reaction Formula 7

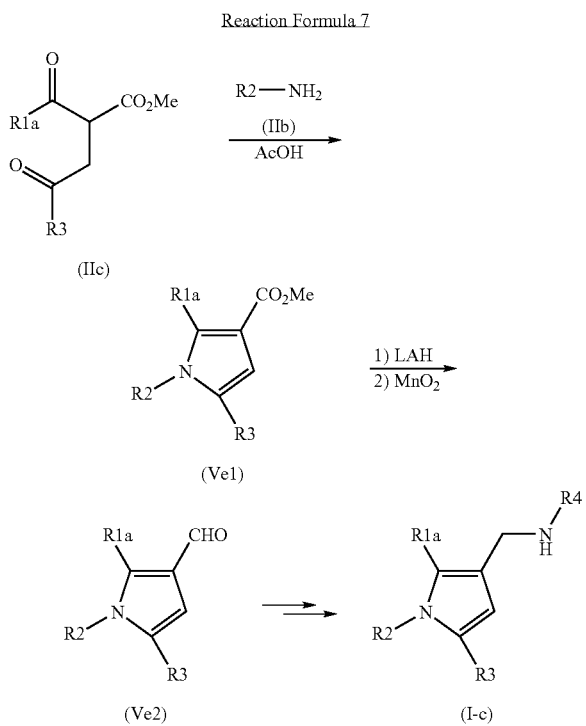

[In the formula, $R^{1a}$, $R^2$, $R^3$ and $R^4$ are the same as above.]

Specifically, a compound of a formula (IIc) is condensed with a compound of a formula (IIb) in acetic acid to obtain a compound of a formula (Ve1).

The amount of the compound of the formula (IIb) to be used may be from 1 to 5 mols, preferably from 1 to 2 mols relative to 1 mol of the compound of the formula (IIc).

The reaction temperature may be from 50 to 100° C., preferably from 60 to 90° C.; and in general, the reaction is completed in 10 minutes to 24 hours.

Next, the ester moiety of the compound of the formula (Ve1) is reduced with lithiumaluminium hydride and then oxidized with manganese dioxide to give a compound of the formula (Ve2), and further, the compound of the formula (Ve2) is reacted according to the production method 1 to obtain a compound of a formula (I-c).

As the compound of the formula (IIc), usable are those described in Examples and commercially-available reagents, and in addition, they may be prepared in conventional known methods.

Other compounds in which $A_1$, $A_2$ and $A_3$ are others than those of the above combinations may also be reacted according to the production methods 1 to 3.

The compound of the formula (I) obtained according to the above-mentioned methods can be readily isolated and purified according to conventional known separation methods. The methods includes, for example, solvent extraction, recrystallization, column chromatography, liquid chromatography, preparative thin-layer chromatography et al.

Depending on the morphology of the substituents therein, the compounds of the invention may exist as stereoisomers and tautomers such as optical isomers, diastereomers, geometric isomers; and the compounds of the invention include all those stereoisomers and tautomers and their mixtures.

Pharmacological Test Example 1

Nociceptin Receptor Binding Inhibition Assay

A cDNA that codes for a human nociceptin receptor gene was cloned into an expression vector pCR3 (by Invitrogen) to prepare pCR3/ORL1. Next, pCR3/ORL1 was transfected in CHO cells using a transfectam (by Nippongene) to obtain a stable expression strain (CHO/ORL1 cells) having resistance against 1 mg/ml G418. Membrane fractions were prepared from this stable expression strain to carry out a receptor binding assay. 11 μg of the membrane fraction, 50 pM [$^{125}$I] Tyr$^{14}$-Nociceptin (by Amersham Pharmacia), 1 mg of wheatgerm agglutinin SPA beads (PVT based, by Amersham Pharmacia) and each test compound were suspended in an NC buffer (50 mM Hepes, 10 mM sodium chloride, 1 mM magnesium chloride, 2.5 mM calcium chloride, 0.1% BSA, 0.025% bacitracin, pH 7.4) and incubated at 37° C. for 60 minutes, and then the radioactivity of the culture was determined. The binding activity to the nociceptin receptor was indicated by the 50% inhibition concentration ($IC_{50}$ value) of [$^{125}$I]Tyr$^{14}$-Nociceptin binding by each test compound. The results were as shown in Table 1.

TABLE 5

| Example | $IC_{50}$ (nM) |
| --- | --- |
| 2 | 0.92 |
| 8 | 7.5 |
| 13 | 8.2 |
| 19 | 0.62 |
| 34 | 1.1 |
| 38 | 6.8 |

Pharmacological Test Example 2

Antagonism Against Nociceptin-Elicited G Protein Activation

CHO cells which stably expressed a nociceptin receptor ORL1 were used to investigate the action of each test compound against nociceptin-elicited G protein activation. A membrane prepared from the CHO/ORL1 cells, 50 nM nociceptin, 200 pM GTPγ[$^{35}$S] (by NEN), 1.5 mg of wheatgerm agglutinin SPA beads (by Amersham Pharmacia) and each test compound were mixed in a GDP buffer (20 mM Hepes, 100 mM sodium chloride, 10 mM magnesium chloride, 1 mM EDTA, 5 μM GDP, pH 7.4) and incubated at 25° C. for 150 minutes, and then the radioactivity was determined. The antagonism against the nociceptin-elicited G protein activation was shown by the 50% inhibition concentration ($IC_{50}$ value) of the test compound against GTPγ[$^{35}$S] binding. The results were as shown in Table 2.

TABLE 2

| Example | $IC_{50}$ (nM) |
| --- | --- |
| 2 | 0.61 |
| 8 | 7.5 |
| 13 | 4.6 |
| 19 | 0.47 |

TABLE 2-continued

| Example | IC$_{50}$ (nM) |
|---------|----------------|
| 34 | 0.6 |
| 38 | 6 |

Pharmaceutical Composition Comprising the Compound of the Formula (I)

The compounds of the invention can be administered orally or parenterally. As formulated into pharmaceutical compositions suitable to administration routes, the compounds of the invention can be used for analgesics against diseases accompanied with pain such as cancerous pain, postoperative pain, migraine, gout, chronic rheumatism, chronic pain and neuralgia; relievers against tolerance to narcotic analgesics such as morphine; relievers against dependence on or addiction to narcotic analgesics such as morphine; analgesic enhancers; antiobesitics or appetite suppressors; treating or prophylactic agents for learning and memory impairment or dementia in aging, cerebrovascular diseases and Alzheimer's disease; agents for treating developmental cognitive abnormality such as attention deficit hyperactivity disorder and learning disability; remedies for schizophrenia; agents for treating neurodegenerative diseases such as Parkinsonism and chorea; anti-depressants or treating agents for affective disorder; treating or prophylactic agents for diabetes insipidus; treating or prophylactic agents for polyuria; remedies for hypotension, etc.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin et al.

Combined with such additives, the compound of the invention may be formulated into solid preparations such as tablets, capsules, granules, powders and suppositories et al; and liquid preparations such as syrups, elixirs, injections et al. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The preparations may contain the compound of the invention in an amount of from 1 to 100% by weight, preferably from 1 to 60% by weight of the preparation. The preparations may further contain any other therapeutically-effective compounds.

In case where the compounds of the invention are used for analgesics against diseases accompanied with pain such as cancerous pain, postoperative pain, migraine, gout, chronic rheumatism, chronic pain and neuralgia; relievers against tolerance to narcotic analgesics such as morphine; relievers against dependence on or addiction to narcotic analgesics such as morphine; analgesic enhancers; antiobesitics or appetite suppressors; treating or prophylactic agents for learning and memory impairment or dementia in aging, cerebrovascular diseases and Alzheimer's disease; agents for treating developmental cognitive abnormality such as attention deficit hyperactivity disorder and learning disability; remedies for schizophrenia; agents for treating neurodegenerative diseases such as Parkinsonism and chorea; anti-depressants or treating agents for affective disorder; treating or prophylactic agents for diabetes insipidus; treating or prophylactic agents for polyuria; remedies for hypotension, then their administration dose and frequency can be varied depending on the sex, the age, the body weight, the degree of symptoms of individual patients and the kind and the extent of the intended therapeutic effect. In general, the dose may be from 0.001 to 50 mg/kg/day, and it may be administered all at a time or may be administered in several times as divided into a few portions. The dose is preferably from about 0.01 to about 25 mg/kg/day, more preferably from about 0.05 to about 10 mg/kg/day.

BEST MODE FOR CARRYING OUT THE INVENTION

The invention is described in detail with reference to the following Examples, to which, however, the invention should not be limited. Unless otherwise specifically indicated, the reagents used in the Examples are all commercial products. In silica gel column chromatography, Wakogel™ C-200 (by Wako Pure Chemical), Wakogel™ C-300 (by Wako Pure Chemical) and Chromatorex NH (by Fuji Silicia) were used. In preparative thin-layer chromatography, Kieselgel 60F$_{254}$ (by Merck) was used. As a chiral column, Chiral Pack AD (by Daicel Chemical) was used. As $^1$H-NMR, JEOL's AL-400-2 (400 MHz) was used, in which tetramethylsilane was used as the standard substance. Mass spectrometra was measured with Waters' Micromass ZQ, according to electrospray ionization method (ESI) or atmospheric chemical ionization (APCI).

Production Example 1

2-(1H-1,2,3-benzotriazol-1-yl)-2-oxoethylacetate

Under a nitrogen atmosphere, thionyl chloride (185 ml) was added at room temperature to a methylene chloride solution (1.2 l) of 1,2,3-benzotriazole (122 g). After stirred for 15 minutes, acetoxyacetic acid (30 g) was added to the reaction solution, and further stirred for 3 hours. The formed precipitate was collected by filtration through a glass filter, and the filtrate was concentrated under reduced pressure. The obtained residue was purified by silica gel column chromatography (hexane/ethyl acetate=9/1 to 7/3 to 6/4) to obtain the entitled compound (53 g) as a white solid.

Production Example 2

1-(5-Fluoro-6-methylpyridin-3-yl)propan-1-one

1) Tert-butyl 2,6-dichloro-5-fluoronicotinate

P-toluenesulfonyl chloride (53.5 g) was added to a pyridine (100 ml)/tert-butanol (300 ml) solution of 2,6-dichloro-5-fluoronicotinic acid (24.5 g), and stirred overnight at room temperature. The reaction liquid was poured into aqueous 10% sodium hydrogencarbonate solution, stirred at room temperature for 2 hours, and then extracted with ethyl acetate.

The extract was washed with saturated saline water, dried with anhydrous magnesium sulfate, the solvent was evaporated off, the obtained residue was purified by silica gel column chromatography (hexane/ethyl acetate=9/1) to obtain the entitled compound (29.5 g).

2) Di-tert-butyl[5-(tert-butoxycarbonyl)-6-chloro-3-fluoropyridin-2-yl]malonate

60% sodium hydride (oil dispersion) (3.34 g) was suspended in dimethylformamide (400 ml), and at 0° C., di-tert-butyl malonate (28.8 g) was added, and stirred at room temperature for 1 hour. A dimethylformamide (100 ml) solution of the compound (29.5 g) obtained in 1) was added to the reaction liquid, and further stirred for 2.5 hours. At 0° C., the reaction liquid was poured into aqueous 10% citric acid solution, and extracted with ethyl acetate. The extract was washed with water and saturated saline water, dried with anhydrous magnesium sulfate, and then the solvent was evaporated off to obtain a crude product of the entitled compound.

3) Di-tert-butyl[5-(tert-butoxycarbonyl)-3-fluoropyridin-2-yl]malonate

Triethylamine (23.2 ml) and active carbon-held palladium hydroxide (6.0 g) were added to an ethanol (500 ml) solution of the compound obtained in 2), and stirred under 1-atmospheric pressure (101.3 KPa) of a hydrogen at room temperature for 7 hours. The insoluble matter was removed by filtration, and the filtrate was concentrated. Ethyl acetate was added to the obtained residue, washed with water and saturated saline water, dried with anhydrous magnesium sulfate, and the solvent was evaporated off to obtain a crude product of the entitled compound.

4) 5-Fluoro-6-methylnicotinic acid

The compound obtained in 3) was added to concentrated hydrochloric acid (200 ml), and stirred overnight at 120° C. The reaction liquid was concentrated under reduced pressure to obtain a crude product of the entitled compound.

5) 5-Fluoro-N-methoxy-N,6-dimethylnicotinamide

1-Ethyl-3-(3-dimethylaminopropyl)carbodiimide hydrochloride (31.9 g) was added to a chloroform (400 ml)/pyridine (130 ml) solution of the compound obtained in 4) and N,O-dimethylhydroxylamine hydrochloride (13.0 g), and stirred overnight at room temperature. Water was added to the reaction liquid, and extracted with chloroform. The extract was washed with saturated saline water, dried with anhydrous magnesium sulfate, the solvent was evaporated off, and the obtained residue was purified by silica gel column chromatography (hexane/ethyl acetate=4/1 to 2/3) to obtain the entitled compound (17.5 g).

6) 1-(5-Fluoro-6-methylpyridin-3-yl)propan-1-one

At 0° C., 1 N ethylmagnesium bromide/tetrahydrofuran solution (100 ml) was added to a tetrahydrofuran (400 ml) solution of the compound (17.5 g) obtained in 5), and stirred at the same temperature for 30 minutes. Aqueous saturated ammonium chloride solution was added to the reaction liquid, and extracted with ethyl acetate. The extract was washed with saturated saline water, dried with anhydrous magnesium sulfate, the solvent was evaporated off, and the obtained residue was purified by silica gel column chromatography (hexane/ethyl acetate=4/1) to obtain the entitled compound (11.7 g).

Production Example 3

4-(5-Fluoro-6-methylpyridin-3-yl)-3-methyl-2,4-dioxobutyl acetate

Under a nitrogen atmosphere at −78° C., lithium hexamethyldisilazide (1.0 M tetrahydrofuran solution, 22.8 ml) was added to a tetrahydrofuran (60 ml) solution of the compound (3.16 g) obtained in Production Example 2. Stirred at −78° C. for 1 hour, the compound (5.39 g) produced in Production Example 1 was added to it. After stirred at room temperature for 1 hour, this was diluted with ethyl acetate, and washed with aqueous saturated ammonium chloride solution. The organic layer was dried with anhydrous sodium sulfate, then the solvent was evaporated off, and the residue was purified by silica gel column chromatography (hexane/ethyl acetate=5/1) to obtain the entitled compound (2.77 g) as a colorless oil.

Production Example 4

4-(3,5-Difluorophenyl)-3-methyl-2,4-dioxobutyl acetate

According to the reaction step of Production Example 3 but using 1-(3,5-difluorophenyl)propan-1-one in place of 1-(5-fluoro-6-methylpyridin-3-yl)propan-1-one, the entitled compound was obtained as a red oil.

Production Example 5

1-(4-Bromo-3,5-difluorophenyl)propan-1-one 1) 2-(3,5-Difluorophenyl)-2-ethyl-1,3-dioxolane Ethylene glycol (773 mg) and a catalytic amount of tosylic acid monohydrate were added to a toluene (20 ml) solution of 1-(3,5-difluorophenyl)propan-1-one (1.06 g). A Dean-Stark tube was attached to the reactor, the reaction liquid was stirred overnight with heating under reflux, then diluted with ethyl acetate, and washed with aqueous saturated sodium hydrogencarbonate solution. The organic layer was dried with anhydrous sodium sulfate, then the solvent was evaporated off, and the residue was purified by silica gel column chromatography (hexane/ethyl acetate=10/1) to obtain the entitled compound (1.31 g) as a colorless oil.

2) 2-(4-Bromo-3,5-difluorophenyl)-2-ethyl-1,3-dioxolane

Under a nitrogen atmosphere at −78° C., n-butyllithium (1.56 M hexane solution, 4.84 ml) was added to a tetrahydrofuran (20 ml) solution of 2-(3,5-difluorophenyl)-2-ethyl-1,3-dioxolane (1.01 g). The reaction liquid was stirred at −78° C. for 15 minutes, then a tetrahydrofuran (10 ml) solution of 1,2-dibromo-1,1,2,2-tetrachloroethane (3.07 g) was added. After stirred at room temperature for 45 minutes, water was added to it, and extracted with chloroform. The organic layer was dried with anhydrous sodium sulfate, then the solvent was evaporated off, and the residue was purified by silica gel column chromatography (hexane/ethyl acetate=50/1) to obtain the entitled compound (1.20 g) as a pale yellow oil.

3) 1-(4-Bromo-3,5-difluorophenyl)propan-1-one 2-(4-Bromo-3,5-difluorophenyl)-2-ethyl-1,3-dioxolane (1.20 g) was dissolved in 1 N hydrochloric acid/tetrahydrofuran/acetic acid (1/1/1, 30 ml). The reaction liquid was stirred overnight with heating under reflux, then diluted with ethyl acetate, and washed with aqueous saturated sodium hydrogencarbonate solution. The organic layer was dried with anhydrous sodium sulfate, then the solvent was evaporated off, and the residue was purified by silica gel column chromatography (hexane/ethyl acetate=10/1) to obtain the entitled compound (806 mg) as a pale yellow oil.

Production Example 6

4-(4-Bromo-3,5-difluorophenyl)-3-methyl-2,4-dioxobutyl acetate

According to the reaction step of Production Example 3 but using the compound obtained in Production Example 5 in place of 1-(5-fluoro-6-methylpyridin-3-yl)propan-1-one, the entitled compound was obtained as a white powder.

Production Example 7

4-(3,4,5-Trifluorophenyl)-3-methyl-2,4-dioxobutyl acetate

According to the reaction step of Production Example 3 but using 1-(3,4,5-trifluorophenyl)propan-1-one in place of 1-(5-fluoro-6-methylpyridin-3-yl)propan-1-one, the entitled compound was obtained.

Production Example 8

4-(3,5-Difluorophenyl)-2,4-dioxobutyl acetate

According to the reaction step of Production Example 3 but using 3,5-difluoroacetophenone in place of 1-(5-fluoro-6-methylpyridin-3-yl)propan-1-one, the entitled compound was obtained.

Production Example 9

4-(3,5-Difluorophenyl)-3-ethyl-2,4-dioxobutyl acetate 1N tetrabutylammonium fluoride/tetrahydrofuran solution (0.5 ml) was added to tetrahydrofran (3 ml) solution of the compound (110 mg) obtained in Production Example 8, and the reaction liquid was concentrated under reduced pressure. The obtained residue was dissolved in chloroform (3 ml), ethyl iodide (52 µl) was added, and stirred overnight at 70° C. 2 N hydrochloric acid was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=4/1) to obtain the entitled compound (36 mg).

Production Example 10

4-(3,5-Difluorophenyl)-3-isopropyl-2,4-dioxobutyl acetate

According to the reaction step of Production Example 9 but using isopropyl iodide in place of ethyl iodide, the entitled compound was obtained.

Production Example 11

Ethyl 4-(6-methylpyridin-3-yl)-2,4-dioxobutyrate

At −78° C., a tetrahydrofuran (5 ml) solution of 5-acetyl-2-picoline (583 mg) was added to a tetrahydrofuran (15 ml) solution of 1 N lithium hexamethyldisilazide/tetrahydrofuran solution (5.2 ml), and stirred at the same temperature for 1 hour. At −78° C., dimethyl oxalate (701 µl) was added to the reaction liquid, and stirred at room temperature for 1 hour. 4 N hydrogen chloride/dioxane solution (4 ml) was added to the reaction liquid, and concentrated under reduced pressure to obtain a crude product of the entitled compound.

Production Example 12

Ethyl 4-(3,5-difluorophenyl)-2,4-dioxobutyrate

According to the reaction step of Production Example 11 but using 3,5-difluoroacetophenone in place of 5-acetyl-2-picoline, the entitled compound was obtained.

Production Example 13

1-(3,5-Difluorophenyl)-4,4-diethoxybutane-1,3-dione

At −78° C., a tetrahydrofuran (20 ml) solution of 3,5-difluoroacetophenone (8.86 g) was added to a tetrahydrofuran (180 ml) solution of 1 N lithium hexamethyldisilazide/tetrahydrofuran solution (68 ml), and stirred at the same temperature for 1 hour. At −78° C., ethyl diethoxyacetate (12.2 ml) was added to the reaction liquid, and stirred overnight at room temperature. At 0° C., 2 N hydrochloric acid (60 ml) was added to the reaction liquid, and extracted with ethyl acetate. The extract was washed with saturated saline water, dried with anhydrous magnesium sulfate, and the solvent was evaporated off to obtain the entitled compound (16.5 g).

Production Example 14

1-(3,4,5-Trifluorophenyl)-4,4-diethoxybutane-1,3-dione

According to the reaction step of Production Example 13 but using 3,4,5-trifluoroacetophenone in place of 3,5-difluoroacetophenone, the entitled compound was obtained.

Production Example 15

1-Tert-butyl-5-(5-fluoro-6-methylpyridin-3-yl)-3-formyl-4-methyl-1H-pyrazole 1) 1-Tert-butyl-5-(5-fluoro-6-methylpyridin-3-yl)-3-hydroxymethyl-4-methyl-1H-pyrazole Tert-butylhydrazine hydrochloride (45 mg) was added to an ethanol (5 ml) solution of the compound (79 mg) obtained in Production Example 3. The reaction liquid was stirred with heating under reflux for 9.5 hours, and then aqueous saturated sodium hydrogencarbonate solution was added, and extracted with chloroform. The organic layer was dried with anhydrous sodium sulfate, the solvent was evaporated off, and the residue was purified by silica gel preparative thin-layer chromatography (chloroform/methanol=10/1) to obtain the entitled compound (34 mg) as a colorless oil.

2) 1-Tert-butyl-5-(5-fluoro-6-methylpyridin-3-yl)-3-formyl-4-methyl-1H-pyrazole

A Dess-Martin's reagent (154 mg) was added to a chloroform (5 ml) solution of the compound (34 mg) obtained in 1). After stirred at room temperature for 20 minutes, this was diluted with ethyl acetate, and washed with aqueous saturated sodium thiosulfate solution and aqueous saturated sodium hydrogencarbonate solution. The organic layer was dried with anhydrous sodium sulfate, then the solvent was evaporated off and the residue was purified by silica gel preparative thin-layer chromatography (hexane/ethyl acetate=1/1) to obtain the entitled compound (30 mg) as a white powder.

Production Example 16

5-(5-Fluoro-6-methylpyridin-3-yl)-3-formyl-1-isopropyl-4-methyl-1H-pyrazole

According to the reaction step of Production Example 15 but using isopropylhydrazine hydrochloride in place of tert-butylhydrazine hydrochloride, the entitled compound was obtained as a colorless oil.

Production Example 17

1,4-Dimethyl-5-(5-fluoro-6-methylpyridin-3-yl)-3-formyl-1H-pyrazole

According to the reaction step of Production Example 15 but using methylhydrazine and 1 N hydrochloric acid in place of tert-butylhydrazine hydrochloride, the entitled compound was obtained as a colorless oil.

Production Example 18

1-Ethyl-5-(5-fluoro-6-methylpyridin-3-yl)-3-formyl-4-methyl-1H-pyrazole

According to the reaction step of Production Example 15 but using ethylhydrazine in place of tert-butylhydrazine hydrochloride, the entitled compound was obtained as a colorless oil.

Production Example 19

5-(5-Fluoro-6-methylpyridin-3-yl)-3-formyl-4-methyl-1-propyl-1H-pyrazole

According to the reaction step of Production Example 15 but using n-propylhydrazine oxalate in place of tert-butylhydrazine hydrochloride, the entitled compound was obtained as a colorless oil.

Production Example 20

1-Cyclopropyl-5-(5-fluoro-6-methylpyridin-3-yl)-3-formyl-1-methyl-1H-pyrazole

According to the reaction step of Production Example 15 but using cyclopropylhydrazine hydrochloride in place of tert-butylhydrazine hydrochloride, the entitled compound was obtained as a colorless oil.

Production Example 21

1-Benzyl-5-(5-fluoro-6-methylpyridin-3-yl)-3-formyl-4-methyl-1H-pyrazole 1) 1-Benzyl-5-(5-fluoro-6-methylpyridin-3-yl)-3-hydroxymethyl-4-methyl-1H-pyrazole Benzylhydrazine hydrochloride (225 mg) was added to an acetic acid (5 ml) solution of the compound (316 mg) obtained in Production Example 3. The reaction liquid was stirred at 90° C. for 1 hour, then the solvent was evaporated off under reduced pressure, the residue was diluted with aqueous saturated sodium hydrogencarbonate solution, and extracted with chloroform. The organic layer was dried with anhydrous sodium sulfate, then the solvent was evaporated off, and the residue was dissolved in methanol/aqueous 1 N sodium hydroxide solution (1/1, 5 ml). After stirred at room temperature for 10 minutes, the reaction liquid was extracted with chloroform. The organic layer was dried with anhydrous sodium sulfate, then the solvent was evaporated off, and the residue was purified by silica gel preparative thin-layer chromatography (chloroform/methanol=10/1) to obtain the entitled compound (373 mg) as a colorless oil.

2) 1-Benzyl-5-(5-fluoro-6-methylpyridin-3-yl)-3-formyl-4-methyl-1H-pyrazole

According to the reaction step of Production Example 15-2) but using the compound obtained in 1), the entitled compound was obtained as a colorless oil.

Production Example 22

5-(3,5-Difluorophenyl)-3-formyl-4-methyl-1H-pyrazole

According to the reaction step of Production Example 15 but using the compound obtained in Production Example 4 in place of 4-(5-fluoro-6-methylpyridin-3-yl)-3-methyl-2,4-dioxobutyl acetate and using hydrazine monohydrate and 4 N hydrogen chloride/dioxane in place of tert-butylhydrazine hydrochloride, the entitled compound was obtained as a brown powder.

Production Example 23

5-(3,5-Difluorophenyl)-1,4-dimethyl-3-formyl-1H-pyrazole

According to the reaction step of Production Example 21 but using the compound obtained in Production Example 4 in place of the compound obtained in Production Example 3 and using methylhydrazine in place of benzylhydrazine hydrochloride, the entitled compound was obtained as a colorless oil.

Production Example 24

1-(2-Cyanoethyl)-5-(3,5-difluorophenyl)-3-formyl-4-methyl-1H-pyrazole

According to the reaction step of Production Example 23 but using 2-cyanoethylhydrazine in place of methylhydrazine, the entitled compound was obtained as a colorless oil.

Production Example 25

5-(3,5-Difluorophenyl)-1-ethyl-3-formyl-4-methyl-1H-pyrazole

According to the reaction step of Production Example 22 but using ethylhydrazine in place of hydrazine monohydrate, the entitled compound was obtained as a colorless oil.

Production Example 26

1-Cyclopropyl-5-(3,5-difluorophenyl)-3-formyl-4-methyl-1H-pyrazole

According to the reaction step of Production Example 22 but using cyclopropylhydrazine hydrochloride in place of hydrazine monohydrate, the entitled compound was obtained as a colorless oil.

Production Example 27

5-(3,5-Difluorophenyl)-3-formyl-1-isopropyl-4-methyl-1H-pyrazole

According to the reaction step of Production Example 15 but using the compound obtained in Production Example 4 in place of 4-(5-fluoro-6-methylpyridin-3-yl)-3-methyl-2,4-dioxobutyl acetate and using isopropylhydrazine hydrochloride in place of tert-butylhydrazine hydrochloride, the entitled compound was obtained as a white powder.

Production Example 28

5-(4-Chloro-3,5-difluorophenyl)-1-ethyl-3-formyl-4-methyl-1H-pyrazole 1) 5-(4-Bromo-3,5-difluorophenyl)-1-ethyl-3-hydroxymethyl-4-methyl-1H-pyrazole According to the reaction step of Production Example 15-1) but using the compound obtained in Production Example 6 in place of 4-(5-fluoro-6-methylpyridin-3-yl)-3-methyl-2,4-dioxobutyl acetate and using ethylhydrazine and 4 N hydrogen chloride/dioxane in place of tert-butylhydrazine hydrochloride, the entitled compound was obtained as a colorless oil.

2) 5-(4-Bromo-3,5-difluorophenyl)-1-ethyl-4-methyl-3-{[tert-butyl(dimethyl)silyl]oxy}methyl-1H-pyrazole Tert-butylchlorodimethylsilane (140 mg) and imidazole (127 mg) were added to a dimethylformamide (5 ml) solution of the compound (154 mg) obtained in 1). After stirred at 80° C. for 90 minutes, this was diluted with ethyl acetate and washed with water. The organic layer was dried with anhydrous sodium sulfate, then the solvent was evaporated off, and the residue was purified by silica gel preparative thin-layer chromatography (hexane/ethyl acetate=20/1) to obtain the entitled compound (212 mg) as a colorless oil.

3) 5-(4-Chloro-3,5-difluorophenyl)-1-ethyl-4-methyl-3-{[tert-butyl(dimethyl)silyl]oxy}methyl-1H-pyrazole Under a nitrogen atmosphere at −78° C., n-butyllithium (1.56 M hexane solution, 0.39 ml) was added to a tetrahydrofuran (5 ml) solution of the compound (207 mg) obtained in 2). The reaction liquid was stirred at −78° C. for 15 minutes, then a tetrahydrofuran (2 ml) solution of hexachloroethane (165 mg) was added. Further, the reaction liquid was stirred at room temperature for 1 hour, then aqueous saturated ammonium chloride solution was added, and extracted with chloroform. The organic layer was dried with anhydrous sodium sulfate, then the solvent was evaporated off, and the residue was purified by silica gel preparative thin-layer chromatography (hexane/ethyl acetate=9/1) to obtain the entitled compound (173 mg) as a colorless oil.

4) 5-(4-Chloro-3,5-difluorophenyl)-1-ethyl-3-hydroxymethyl-4-methyl-1H-pyrazole

1 N tetrabutylammonium fluoride/tetrahydrofuran solution (863 μL) was added to a tetrahydrofuran (5 ml) solution of the compound (173 mg) obtained in 3). The reaction liquid was stirred overnight at room temperature, then the solvent was evaporated off, and the residue was purified by NH-silica gel preparative thin-layer chromatography (hexane/ethyl acetate=1/2) to obtain the entitled compound (113 mg) as a white powder.

5) 5-(4-Chloro-3,5-difluorophenyl)-1-ethyl-3-formyl-4-methyl-1H-pyrazole

According to the reaction step of Production Example 15-2) but using the compound obtained in 4) in place of 5-(5-fluoro-6-methylpyridin-3-yl)-3-hydroxymethyl-4-methyl-1-tert-butyl-1H-pyrazole, the entitled compound (115 mg) was obtained as a colorless oil.

Production Example 29

1,4-Dimethyl-3-formyl-5-(3,4,5-trifluorophenyl)-1H-pyrazole

According to the reaction step of Production Example 23 but using the compound obtained in Production Example 7 in place of the compound obtained in Production Example 4, the entitled compound was obtained.

Production Example 30

5-(3,5-Difluorophenyl)-4-ethyl-3-formyl-1-methyl-1H-pyrazole 1) 5-(3,5-Difluorophenyl)-4-ethyl-3-hydroxymethyl-1-methyl-1H-pyrazole According to the reaction step of Production Example 15-1) but using the compound obtained in Production Example 9 in place of 4-(5-fluoro-6-methylpyridin-3-yl)-3-methyl-2,4-dioxobutyl acetate and using methylhydrazine and 4 N hydrogen chloride/dioxane in place of tert-butylhydrazine hydrochloride, the entitled compound was obtained.

2) 5-(3,5-Difluorophenyl)-1-dimethyl-4-ethyl-3-formyl-1H-pyrazole

Manganese dioxide (100 mg) was added to a chloroform (2 ml) solution of the compound (22 mg) obtained in 1), and stirred at room temperature for 3 hours. The insoluble matter was removed by filtration, and the filtrate was concentrated to obtain a crude product of the entitled compound.

Production Example 31

5-(3,5-Difluorophenyl)-3-formyl-4-isopropyl-1-methyl-1H-pyrazole

According to the reaction step of Production Example 30 but using the compound obtained in Production Example 10 in place of the compound obtained in Production Example 9, the entitled compound was obtained.

Production Example 32

4-Chloro-5-(3,5-difluorophenyl)-3-formyl-1-methyl-1H-pyrazole

1) 3-Acetoxymethyl-5-(3,5-difluorophenyl)-1-methyl-1H-pyrazole

The compound (322 mg) obtained in Production Example 8 and methylhydrazine (74 µl) were dissolved in acetic acid (3 ml), and stirred at 80° C. for 1 hour. The reaction liquid was concentrated under reduced pressure, and the obtained residue was diluted with ethyl acetate. The solution was washed with aqueous saturated sodium hydrogencarbonate solution and saturated saline water, dried with anhydrous magnesium sulfate, the solvent was evaporated off, and the obtained residue was purified by silica gel column chromatography (hexane/ethyl acetate=10/1 to 2/1) to obtain the entitled compound (144 mg).

2) 3-Acetoxymethyl-4-chloro-5-(3,5-difluorophenyl)-1-methyl-1H-pyrazole

The compound (39 mg) obtained in 1) and N-chlorosuccinimide (30 mg) were dissolved in acetonitrile (1 ml), and stirred overnight at 80° C. N-chlorosuccinimide (10 mg) was added to the reaction liquid, and further stirred at 80° C. for 7 hours. Water was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=2/1) to obtain the entitled compound (42 mg).

3) 4-Chloro-5-(3,5-difluorophenyl)-3-hydroxymethyl-1-methyl-1H-pyrazole

Aqueous 1 N sodium hydroxide solution (1 ml) was added to a methanol (2 ml) solution of the compound (42 mg) obtained in 2), and stirred at room temperature for 2 hours. Water was added to the reaction liquid, and extracted with chloroform. The extract was dried with anhydrous magnesium sulfate, and the solvent was evaporated off to obtain a crude product of the entitled compound.

4) 4-Chloro-5-(3,5-difluorophenyl)-3-formyl-1-methyl-1H-pyrazole

According to the reaction step of Production Example 30-2) but using the compound obtained in 3) in place of 5-(3,5-difluorophenyl)-4-ethyl-3-hydroxymethyl-1-methyl-1H-pyrazole, the entitled compound was obtained.

Production Example 33

4-Ethyl-3-formyl-1-methyl-5-(6-methylpyridin-3-yl)-1H-pyrazole

1) 3-Ethoxycarbonyl-1-methyl-5-(6-methylpyridin-3-yl)-1H-pyrazole

According to the reaction step of Production Example 15-1) but using the compound obtained in Production Example 11 in place of 4-(5-fluoro-6-methylpyridin-3-yl)-3-methyl-2,4-dioxobutyl acetate and using methylhydrazine in place of tert-butylhydrazine hydrochloride, the entitled compound was obtained.

2) 4-Bromo-3-ethoxycarbonyl-1-methyl-5-(6-methylpyridin-3-yl)-1H-pyrazole

The compound (283 mg) obtained in 1) and N-bromosuccinimide (411 mg) were dissolved in acetonitrile (4 ml), and stirred overnight at 80° C. Aqueous saturated sodium hydrogencarbonate solution was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=4/1 to 0/100) to obtain the entitled compound (331 mg).

3) 3-Ethoxycarbonyl-1-methyl-5-(6-methylpyridin-3-yl)-4-vinyl-1H-pyrazole

Tributyl(vinyl)tin (216 µl) and tetrakis(triphenylphosphine)palladium (28 mg) were added to a toluene (3 ml) solution of the compound (160 mg) obtained in 2), and stirred overnight at 110° C. Aqueous 10% potassium fluoride solution was added to the reaction liquid, then stirred at room temperature for 1 hour, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=4/1 to 0/100) to obtain the entitled compound (119 mg).

4) 3-Ethoxycarbonyl-4-ethyl-1-methyl-5-(6-methylpyridin-3-yl)-1H-pyrazole

The compound (119 mg) obtained in 3) and active carbon-held palladium (30 mg) were suspended in ethanol (3 ml), and stirred under 1-atmospheric pressure (101.3 KPa) of a hydrogen at room temperature for 2 days. The insoluble matter was removed by filtration, the filtrate was concentrated to obtain a crude product of the entitled compound.

5) 4-Ethyl-3-hydroxymethyl-1-methyl-5-(6-methylpyridin-3-yl)-1H-pyrazole

At 0° C., lithiumaluminium hydride (25 mg) was added to a tetrahydrofuran (3 ml) solution of the compound obtained in 4), and stirred at the same temperature for 30 minutes. Sodium sulfate 10-hydrate was added to the reaction liquid, and stirred overnight at room temperature. The insoluble matter was removed by filtration, and the filtrate was concentrated to obtain a crude product of the entitled compound.

6) 4-Ethyl-3-formyl-1-methyl-5-(6-methylpyridin-3-yl)-1H-pyrazole

According to the reaction step of Production Example 30-2) but using the compound obtained in 5) in place of 5-(3,5-difluorophenyl)-4-ethyl-3-hydroxymethyl-1-methyl-1H-pyrazole, the entitled compound was obtained.

Production Example 34

4-Vinyl-5-(3,5-difluorophenyl)-3-formyl-1-methyl-1H-pyrazole

According to the reaction step of Production Example 33-1) to 3), 5) and 6) but using the compound obtained in Production Example 12 in place of the compound obtained in Production Example 11, the entitled compound was obtained.

Production Example 35

3-Formyl-4-methoxymethyl-1-methyl-5-(6-methylpyridin-3-yl)-1H-pyrazole

1) 4-Vinyl-3-hydroxymethyl-1-methyl-5-(6-methylpyridin-3-yl)-1H-pyrazole

At 0° C., lithiumaluminium hydride (32 mg) was added to a tetrahydrofuran (4 ml) solution of the compound (152 mg) obtained in Production Example 33-3), and stirred at the same temperature for 15 minutes. Sodium sulfate 10-hydrate was added to the reaction liquid, and stirred overnight at room temperature. The insoluble matter was removed by filtration, and the filtrate was concentrated to obtain a crude product of the entitled compound.

2) 3-{[3-Tert-butyl(dimethyl)silyl]oxy}methyl-1-methyl-5-(6-methylpyridin-3-yl)-4-vinyl-1H-pyrazole Tert-butyldimethylchlorosilane (101 mg) and imidazole (91 mg) were added to a dimethylformamide (2 ml) solution of the compound obtained in 1), and stirred at room temperature for 45 minutes. Water was added to the reaction liquid, and extracted with ethyl acetate. The extract was washed with water and saturated saline water, dried with anhydrous magnesium sulfate, the solvent was evaporated off, and the obtained residue was purified by silica gel column chromatography (hexane/ethyl acetate=4/1 to 1/2) to obtain the entitled compound (143 mg).

3) 3-{[3-Tert-butyl(dimethyl)silyl]oxy}methyl-1-methyl-5-(6-methylpyridin-3-yl)-4-formyl-1H-pyrazole Aqueous 1% osmium tetraoxide solution (3 drops) was added to a tetrahydrofuran (3 ml)/water (3 ml) suspension of the compound (143 mg) obtained in 2) and sodium periodate (225 mg), and stirred at room temperature for 2 hours. Aqueous 10% sodium sulfite solution was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=9/1 to 1/2) to obtain the entitled compound (97 mg).

4) 3-{[3-Tert-butyl(dimethyl)silyl]oxy}methyl-1-methyl-5-(6-methylpyridin-3-yl)-4-hydroxymethyl-1H-pyrazole Sodium borohydride (12 mg) was added to a methanol (2 ml) solution of the compound (71 mg) obtained in 3), and stirred at room temperature for 30 minutes. Water was added to the reaction liquid, and extracted with ethyl acetate. The extract was washed with saturated saline water, dried with anhydrous magnesium sulfate, and the solvent was evaporated off to obtain a crude product of the entitled compound.

5) 3-{[3-Tert-butyl(dimethyl)silyl]oxy}methyl-1-methyl-5-(6-methylpyridin-3-yl)-4-hydroxymethyl-1H-pyrazole At 0° C., 60% sodium hydride (oil dispersion) (13 mg) was added to a tetrahydrofuran (2 ml) solution of the crude product obtained in 4), and stirred at the same temperature for 10 minutes. At 0° C., methyl iodide (14 µl) was added to the reaction liquid, and stirred overnight at room temperature. Water was added to the reaction liquid, and extracted with ethyl acetate. The extract was washed with saturated saline water, dried with anhydrous magnesium sulfate, then the solvent was evaporated off and the obtained residue was purified by silica gel column chromatography (hexane/ethyl acetate=4/1 to 1/2) to obtain the entitled compound (17 mg).

6) 3-Hydroxymethyl-4-methoxymethyl-1-methyl-5-(6-methylpyridin-3-yl)-1H-pyrazole 1N tetrabutylammonium fluoride/tetrahydrofuran solution (0.1 ml) was added to a tetrahydrofuran (1 ml) solution of the compound (17 mg) obtained in 5), and stirred at room temperature for 1 hour. Aqueous saturated sodium hydrogencarbonate solution was added to the reaction liquid, and extracted with ethyl acetate. The extract was washed with water and saturated saline water, then dried with anhydrous magnesium sulfate, the solvent was evaporated off, and the obtained residue was purified by silica gel preparative thin-layer chromatography (chloroform/methanol=10/1) to obtain the entitled compound (7 mg).

7) 3-Formyl-4-methoxymethyl-1-methyl-5-(6-methylpyridin-3-yl)-1H-pyrazole

According to the reaction step of Production Example 30-2) but using the compound obtained in 6) in place of 5-(3,5-difluorophenyl)-4-ethyl-3-hydroxymethyl-1-methyl-1H-pyrazole, the entitled compound was obtained.

Production Example 36

5-(3,5-Difluorophenyl)-3-formyl-4-methoxymethyl-1-{[2-(trimethylsilyl)ethoxy]methyl}-1H-pyrazole

1) 3-Diethoxymethyl-5-(3,5-difluorophenyl)-1H-pyrazole

Hydrazine monohydrate (3.03 ml) was added to an ethanol (100 ml) solution of the compound (16.5 g) obtained in Production Example 13, and stirred at room temperature for 2 hours. The reaction liquid was concentrated under reduced pressure, and ethyl acetate was added to the obtained residue. The solution was washed with saturated saline water, dried with anhydrous magnesium sulfate, then the solvent was evaporated off, and the obtained residue was purified by silica gel column chromatography (hexane/ethyl acetate=3/1) to obtain the entitled compound (14.0 g).

2) 3-Diethoxymethyl-5-(3,5-difluorophenyl)-1-{[2-(trimethylsilyl)ethoxy]methyl}-1H-pyrazole At 0° C., 60% sodium hydride (oil dispersion) (2.39 g) was added to a tetrahydrofuran (250 ml) solution of the compound (14.0 g) obtained in 1), and stirred at the same temperature for 10 minutes. At 0° C., 2-(trimethylsilyl)ethoxymethyl chloride (10.5 ml) was added to the reaction liquid, and stirred at room temperature for 40 minutes. The reaction liquid was poured into water with ice, and extracted with ethyl acetate. The extract was washed with saturated saline water, dried with anhydrous magnesium sulfate, then the solvent was evaporated off to obtain a crude product of the entitled compound.

3) 4-Bromo-3-diethoxymethyl-5-(3,5-difluorophenyl)-1-{[2-(trimethylsilyl)ethoxy]methyl}-1H-pyrazole According to the reaction step of Production Example 33-2) but using the compound obtained in 2) in place of 3-ethoxycarbonyl-1-methyl-5-(6-methylpyridin-3-yl)-1H-pyrazole, the entitled compound was obtained.

4) 3-Diethoxymethyl-5-(3,5-difluorophenyl)-4-methoxymethyl-1-{[2-(trimethylsilyl)ethoxy]methyl}-1H-pyrazole At −78° C., 1.58 M n-butyllithium/hexane solution (17.9 ml) was added to a diethyl ether (120 ml) solution of the compound (13.9 g) obtained in 3), and stirred at the same temperature for 20 minutes. At −78° C., chloromethyl methyl ether (2.3 ml) was added to the reaction liquid, and stirred at room temperature for 1 hour. Aqueous saturated sodium hydrogencarbonate solution was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=10/1 to 7/1) to obtain the entitled compound (7.59 g).

5) 5-(3,5-difluorophenyl)-3-formyl-4-methoxymethyl-1-{[2-(trimethylsilyl)ethoxy]methyl}-1H-pyrazole The compound (7.59 g) obtained in 4) and p-toluenesulfonic acid monohydrate (158 mg) were dissolved in acetone (80 ml) and water (20 ml), and stirred overnight at room temperature. Aqueous saturated sodium hydrogencarbonate solution was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=10/1) to obtain the entitled compound (5.12 g).

Production Example 37

5-(3,4,5-Trifluorophenyl)-3-formyl-4-methoxymethyl-1-{[2-(trimethylsilyl)ethoxy]methyl}-1H-pyrazole 1) 4-Bromo-3-diethoxymethyl-5-(3,4,5-trifluorophenyl)-1-{[2-(trimethylsilyl)ethoxy]methyl}-1H-pyrazole According to the reaction step of Production Example 36-1) to 3) but using the compound obtained in Production Example 14 in place of the compound obtained in Production Example 13, the entitled compound was obtained as a white solid.

2) 4-Vinyl-3-diethoxymethyl-5-(3,4,5-trifluorophenyl)-1-{[2-(trimethylsilyl)ethoxy]methyl}-1H-pyrazole According to the reaction step of Production Example 33-3) but using the compound obtained in 1), the entitled compound was obtained as a pale yellow oil.

3) 4-Methoxymethyl-3-diethoxymethyl-5-(3,4,5-trifluorophenyl)-1-{[2-(trimethylsilyl)ethoxy]methyl}-1H-pyrazole According to the reaction step of Production Example 35-3) to 5) but using the compound obtained in 2), the entitled compound was obtained as a pale yellow oil.

4) 4-Methoxymethyl-3-formyl-5-(3,4,5-trifluorophenyl)-1-{[2-(trimethylsilyl)ethoxy]methyl}-1H-pyrazole According to the reaction step of Production Example 36-5) but using the compound obtained in 3), the entitled compound was obtained as a colorless amorphous substance.

Production Example 38

1-(3,5-Difluorophenyl)-5-ethyl-4-formyl-2-methyl-imidazole 1) 1-(3,5-Difluorophenyl)-4-ethoxycarbonyl-2-methyl-imidazole 3,5-Difluoroaniline (6.75 g), ethyl nitroacetate (5.85 ml), ethyl orthoformate (9.56 ml) and acetic acid (1.2 ml) were mixed, and stirred under heating at 120° C. for 1 hour. The reaction liquid was left cooled, and the precipitated solid was collected by filtration using hexane/ethanol (1/1). Ethanol (140 ml), ethyl orthoacetate (19.1 ml) and mercury(II) chloride (714 mg) were added to the obtained solid (14.3 g). With further stirring, aluminium foil (2.84 g) was added little by little. After all the aluminium foil was dissolved, this was further stirred under heat at 80° C. for 4 hours. The reaction liquid was left cooled, then poured into a mixture of ethyl acetate and water, and the precipitated solid was removed by filtration through Celite. The filtrate was extracted with ethyl acetate, the organic layer was dried with magnesium sulfate and concentrated under reduced pressure. The obtained residue was purified by silica gel column chromatography (ethyl acetate/hexane=2/1) to obtain the entitled compound (8.50 g) as a pale brown solid.

2) 5-Bromo-1-(3,5-difluorophenyl)-4-ethoxycarbonyl-2-methyl-imidazole

According to the reaction step of Production Example 33-2) but using the compound obtained in 1), the entitled compound was obtained as a pale brown solid.

3) 1-(3,5-Difluorophenyl)-5-ethyl-4-formyl-2-methylimidazole

According to the reaction step of Production Example 33-3) to 6) but using the compound obtained in 2), the entitled compound was obtained as a pale brown solid.

Production Example 39

1-(3,5-Difluorophenyl)-4-formyl-5-isopropyl-2-methyl-imidazole

The reaction step of Production Example 33-3) in which, however, used were the compound obtained in Production Example 38-2) and tributyl(isopropenyl)tin in place of tributyl(vinyl)tin, followed by the reaction step of Production Example 33-4) to 6) gave the entitled compound as a white solid.

Production Example 40

5-(2,4-Dichlorophenyl)-1-(3,5-difluorophenyl)-4-formyl-2-methyl-imidazole 1) 5-(2,4-Dichlorophenyl)-1-(3,5-difluorophenyl)-4-ethoxycarbonyl-2-methyl-imidazole The compound (270 mg) obtained in Production Example 38-2) was dissolved in dioxane (4 ml), then 2,4-dichlorophenylboronic acid (150 mg), tetrakis-triphenylphosphine palladium(0) (40 mg) and aqueous 0.8 M sodium carbonate solution (1.6 ml) were added, and stirred under heating under a nitrogen atmosphere at 100° C. for 12 hours. The reaction liquid was left cooled and then poured into water and ethyl acetate for separation of the organic layer, and the organic layer was dried with magnesium sulfate and concentrated under reduced pressure. The obtained residue was purified by silica gel thin-layer chromatography (ethyl acetate/hexane=3/1) to obtain the entitled compound (80 mg) as a pale yellow oil.

2) 5-(2,4-Dichlorophenyl)-1-(3,5-difluorophenyl)-4-formyl-2-methyl-imidazole

According to the reaction step of Production Example 33-5) and 6) but using the compound obtained in 1), the entitled compound was obtained.

Production Example 41

1-(3,5-Difluorophenyl)-2-ethyl-5-methyl-3-formyl-1H-pyrrole 1) 1-(3,5-Difluorophenyl)-3-ethoxycarbonyl-2-ethyl-5-methyl-1H-pyrrole Ethyl 3-oxo-2-(2-oxopropyl)pentanoate (200 mg) and 3,5-difluoroaniline (380 mg) were dissolved in acetic acid (10 mL), and stirred at 80° C. for 2.5 hours. The reaction liquid was cooled to room temperature, then the solvent was evaporated off, the residue was diluted with chloroform, and washed with aqueous saturated sodium hydrogencarbonate solution. The extract was washed with saturated saline water, then dried with anhydrous sodium sulfate, then the solvent was evaporated off, and the obtained residue was purified by silica gel column chromatography (hexane/ethyl acetate=10/1) to obtain the entitled compound (287 mg) as a pale yellow oil.

2) 1-(3,5-Difluorophenyl)-2-ethyl-5-methyl-3-formyl-1H-pyrrole

According to the reaction step of Production Example 33-5) and 6) but using the compound obtained in 1), the entitled compound was obtained as a colorless oil.

Production Example 42

1-(3,5-Difluorophenyl)-2-methoxymethyl-5-methyl-3-formyl-1H-pyrrole

According to the reaction step of Production Example 41 but using methyl 2-methoxyacetyl-4-oxopentanoate in place of ethyl 3-oxo-2-(2-oxopropyl)pentanoate, the entitled compound was obtained as a brown solid.

Production Example 43

(1S,3R)-3-fluorocyclopentylamine hydrochloride 1) (1R,4R)-4-acetoxy-1-phthalimide-2-cyclopentene At 0 to 5° C., diethyl azodicarboxylate (261 g) was added to a tetrahydrofuran (6.8 l) solution of (1R,4S)-(+)-2-cyclopentene-1,4-diol 1-acetate (190 g), phthalimide (220 g) and triphenyl phosphine (393 g), and stirred at room temperature for 4 hours. The reaction liquid was concentrated under reduced pressure, then diethyl ether (1 l) and hexane (2l) were added to the obtained residue, and stirred at room temperature for 30 minutes. The reaction liquid was filtered, washed with hexane, and the obtained residue was purified by silica gel column chromatography (dichloromethane) to obtain the entitled compound (307 g).

2) (1S,3S)-3-acetoxy-1-phthalimidocyclopentane

The compound (297 g) obtained in 1) and active carbon-held palladium hydroxide (29.7 g) were suspended in methanol (4 l), and stirred under 1-atmospheric pressure (101.3 KPa) of a hydrogen at room temperature for 4 hours. The insoluble matter was removed by filtration, and the filtrate was concentrated to obtain the entitled compound (287 g).

3) (1S,3S)-3-acetoxy-1-aminocyclopentane

The compound (287 g) obtained in 2) and hydrazine monohydrate (78.9 g) were dissolved in ethanol (5.8 l), and heated under reflux for 3 hours. The insoluble matter was removed by filtration, the filtrate was concentrated. Dichloromethane (8.6 l) was added to the obtained residue, and the insoluble matter was removed by filtration. The filtrate was washed with saturated saline water, dried with anhydrous magnesium sulfate, and the solvent was evaporated off to obtain the entitled compound (122 g).

4) (1S,3S)-3-acetoxy-1-{[(benzyloxy)carbonyl]amino}cyclopentane

The compound (122 g) obtained in 3), benzyl chloroformate (218 g) and sodium hydrogencarbonate (143 g) were suspended in water (2.44 l) and dioxane (2.44 l), and stirred at room temperature for 3 hours. The reaction liquid was extracted with ethyl acetate. The extract was washed with saturated saline water, dried with anhydrous magnesium sulfate, then the solvent was evaporated off to obtain a crude product of the entitled compound.

5) (1S,3S)-1-{[(benzyloxy)carbonyl]amino}-3-hydroxycyclopentane

Water (1.15 l) and lithium hydroxide monohydrate (53.6 g) were added to an ethanol (3.45 l) solution of the compound obtained in 4), and stirred at room temperature for 3 hours. The reaction liquid was concentrated under reduced pressure, and ethyl acetate was added to the obtained residue. The solution was washed with saturated saline water, dried with anhydrous magnesium sulfate, and the solvent was evaporated off to obtain the entitled compound (183 g).

6) (1S,3S)-1-{[(benzyloxy)carbonyl]amino}-3-[(methylsulfonyl)oxy]cyclopentane At 0° C., methanesulfonyl chloride (107 g) was added to a dichloromethane (2.8 l) solution of the compound (183 g) obtained in 5) and triethylamine (118 g), and stirred at room temperature for 1.5 hours. The reaction liquid was washed with aqueous saturated sodium hydrogencarbonate solution, then concentrated under reduced pressure, and ethyl acetate was added to the obtained residue. The solution was washed with saturated saline water, dried with anhydrous magnesium sulfate, and the solvent was evaporated off to obtain the entitled compound (200 g).

7) (1S,3R)-1-{[(benzyloxy)carbonyl]amino}-3-fluoro-cyclopentane

The compound (200 g) obtained in 6) and tetrabutylammonium fluoride trihydrate (334 g) were dissolved in acetonitrile (4.4 l), and heated under reflux for 1 hour. Aqueous saturated sodium hydrogencarbonate solution was added to the reaction liquid, and extracted with ethyl acetate. The extract was washed with saturated saline water, dried with anhydrous magnesium sulfate, then the solvent was evaporated off, and the obtained residue was purified by silica gel column chromatography (hexane/ethyl acetate=6/1) to obtain the entitled compound (98.8 g).

8) (1S,3R)-3-fluorocyclopentylamine hydrochloride

The compound (98.8 g) obtained in 7) and active carbon-held palladium hydroxide (29.7 g) were suspended in methanol (4 l), and stirred under 1-atmospheric pressure (101.3 KPa) of a hydrogen at room temperature for 20 hours. The insoluble matter was removed by filtration, then 4 N hydrogen chloride/dioxane solution (126 ml) was added to the filtrate, and the solvent was evaporated off. The obtained residue was recrystallized from ethanol/hexane to obtain the entitled compound (50.2 g).

Production Example 44

(1S,2R)-2-fluorocyclopentylamine hydrochloride

1) Trans-2-fluorocyclopentanol

Triethylamine trihydrofluoride (95.8 g) was added to a mixture of triethylamine (166 ml) and 6-oxobicyclo[3.1.0]hexane (25 g), heated up to 100° C., and stirred at the same temperature for 3 days. With cooling with ice, water (200 ml) was added to the reaction mixture, and extracted three times with diethyl ether (400 ml). The combined organic layers were washed three times with water, twice with 1 N hydrochloric acid and saturated saline water, and then dried with anhydrous sodium sulfate added thereto. Sodium sulfate was removed by filtration, the filtrate was concentrated under reduced pressure to obtain a crude product (24.8 g) of the entitled compound as a pale yellow oil.

2) (1S,2R)-2-fluoro-1-phthalimidocyclopentane

Triphenyl phosphine (93.6 g) and phthalimide (52.6 g) were added to a tetrahydrofuran solution (500 ml) of the compound (24.8 g) obtained in 1). With cooling with ice, diisopropyl azodicarboxylate (70.8 ml) was added to the reaction solution, and then heated up to room temperature. At the same temperature, this was stirred for 3 hours, and then aqueous saturated sodium hydrogencarbonate solution was added thereto to stop the reaction. The mixture was extracted twice with ethyl acetate, the combined organic layers were washed with water and saturated saline water, and dried with anhydrous sodium sulfate added thereto. Sodium sulfate was removed by filtration, the filtrate was concentrated under reduced pressure, and the obtained residue was purified by silica gel column chromatography (hexane/ethyl acetate=100/0 to 85/15) to obtain a racemate (38.6 g) of the entitled compound as a pale yellow solid. The racemic product was optically resolved in a chiral column (Chiral Pack AD, hexane/ethanol=9/1+0.1% diethylamine) to obtain a chiral form of the entitled compound (15.9 g, >99.9% ee) as a pale yellow solid.

3) (1S,2R)-2-fluorocyclopentylamine hydrochloride

Concentrated hydrochloric acid (300 ml) was added to the compound (15.9 g) obtained in 2), heated at 120° C. and stirred overnight. The reaction liquid was stirred with cooling with ice for 2 hours, then the formed percipitate was removed by filtration, and the filtrate was washed three times with chloroform (300 ml). The aqueous layer was concentrated under reduced pressure, then the obtained residue was dissolved in methanol (80 ml), and diethyl ether (320 ml) was gradually added to the solution. The formed precipitate was collected by filtration with washing with diisopropyl ether to obtain the entitled compound (6.94 g) as a white solid.

Production Example 45

Cis-4-fluorocyclohexylamine hydrochloride

1) Benzyl (trans-4-hydroxycyclohexyl)carbamate

Trans-4-hydroxycyclohexylamine (23 g) was dissolved in 1,4-dioxane (360 ml) and water (360 ml), and cooled at 0° C.

Aqueous 5 N sodium hydroxide solution (160 ml) and benzyl chloroformate (72 ml) were added to the reaction liquid successively, then restored to room temperature and stirred for 64 hours. The white solid formed in the reaction system was collected by filtration, then successively washed with water and ethyl acetate, and dried at 50° C. under reduced pressure to obtain the entitled compound (32.3 g) as a white solid.

2) Benzyl (cis-4-fluorocyclohexyl)carbamate

Under a nitrogen atmosphere, the compound (13.7 g) obtained in 1) was suspended in chloroform (140 ml), and [bis(2-methoxyethyl)amino]sulfur trifluoride (11.6 ml) was dropwise added to the reaction liquid, and stirred for 30 minutes. Water was added to the reaction liquid, extracted with chloroform, and the extract was washed with saturated saline water, dried with anhydrous magnesium sulfate, and the solvent was evaporated off. The obtained residue was purified by silica gel column chromatography (hexane/ethyl acetate=9/1 to 1/1) to obtain the entitled compound (1.30 g) as a white solid.

3) Cis-4-fluorocyclohexylamine hydrochloride

The compound (1.30 g) obtained in 2) was dissolved in methanol (40 ml), then 10% palladium(II) hydroxide/carbon (300 mg) was added, and stirred under a hydrogen atmosphere at room temperature for 5 hours. The reaction liquid was filtered, then 10% hydrogen chloride/methanol solution (10 ml) was added, and the solvent was evaporated off. The formed residue was solidified with ethanol/heptane mixture to obtain the entitled compound (307 mg) as a white solid.

Production Example 46

5-(4-Chloro-3,5-difluorophenyl)-3-formyl-4-methoxymethyl-1H-pyrazole

1) 5-(4-Chloro-3,5-difluorophenyl)-3-diethoxymethyl-4-methoxymethyl-1-{[2-(trimethylsilyl)ethoxy]methyl}-1H-pyrazole At −78° C., 1.58 M n-butyllithium/hexane solution (0.39 ml) was added to a THF (8 ml) solution of the compound (216 mg) obtained in Production Example 36-4), and stirred at the same temperature for 15 minutes. At −78° C., hexachloroethane (224 mg) in THF (2 ml) was added to the reaction liquid, and stirred at room temperature for 1 hour and 20 minutes. Aqueous saturated ammonium chloride solution was added to the reaction liquid, and extracted with chloroform. The extract was washed with saturated saline water, dried with anhydrous magnesium sulfate, the solvent was evaporated off, and the obtained residue was purified by silica gel column chromatography (hexane/ethyl acetate=5/1) to obtain the entitled compound (232 mg).

2) 5-(4-Chloro-3,5-difluorophenyl)-3-formyl-4-methoxymethyl-1H-pyrazole

The compound obtained in 1) was dissolved in trifluoroacetic acid (4.5 ml) and water (0.5 ml), and stirred at room temperature for 3 hours. Aqueous 5 N sodium hydroxide solution was added to the reaction liquid, and extracted with methylene chloride. The extract was washed with saturated saline water, dried with anhydrous magnesium sulfate, and the solvent was evaporated off to obtain the entitled compound (136 mg).

Example 1

1-Tert-butyl-3-[(1S,3R)-3-fluorocyclopentylamino]methyl-5-(5-fluoro-6-methylpyridin-3-yl)-4-methyl-1H-pyrazole The compound (18 mg) obtained in Production Example 43 and zinc biscyanoborohydride (0.3 M methanol solution, 1.09 ml) were added to a methanol (1 ml) solution of the compound (30 mg) obtained in Production Example 15. The reaction liquid was stirred at room temperature for 2 hours, then diluted with ethyl acetate, and washed with aqueous saturated sodium hydrogencarbonate solution. The organic layer was dried with anhydrous sodium sulfate, then the solvent was evaporated off, and the residue was purified by NH-silica gel preparative thin-layer chromatography (hexane/ethyl acetate=1/1) to obtain the entitled compound (29 mg) as a colorless oil.

$^1$H-NMR (CDCl$_3$) δ=1.41 (9H, s), 1.74 (3H, s), 1.81 (4H, m), 2.03 (2H, m), 2.22 (1H, m), 2.60 (3H, d, J=2.9 Hz), 3.26 (1H, m), 3.73 (1H, d, J=13.0 Hz), 3.77 (1H, d, J=13.0 Hz), 5.13 (1H, m), 7.24 (1H, m), 8.22 (1H, s)

ESI-MS (+20 eV) m/z 363.2 [M+H]$^+$

Example 2

3-[(1S,3R)-3-fluorocyclopentylamino]methyl-5-(5-fluoro-6-methylpyridin-3-yl)-1-isopropyl-4-methyl-1H-pyrazole According to the reaction step of Example 1 but using the compound obtained in Production Example 16 in place of the compound obtained in Production Example 15, the entitled compound was obtained.

$^1$H-NMR (CDCl$_3$) δ=1.41 (6H, d, J=6.7 Hz), 1.80 (4H, m), 1.96 (3H, s), 2.03 (2H, m), 2.21 (1H, m), 2.60 (3H, d, J=1.0 Hz), 3.25 (1H, m), 3.76 (1H, d, J=13.3 Hz), 3.80 (1H, d, J=13.3 Hz), 4.27 (1H, m), 5.13 (1H, m), 7.25 (1H, d, J=9.8 Hz), 8.24 (1H, s)

ESI-MS (+20 eV) m/z 349.2 [M+H]$^+$

Example 3

1,4-Dimethyl-3-[(1S,3R)-3-fluorocyclopentylamino]methyl-5-(5-fluoro-6-methylpyridin-3-yl)-1H-pyrazole According to the reaction step of Example 1 but using the compound obtained in Production Example 17 in place of the compound obtained in Production Example 15, the entitled compound was obtained.

$^1$H-NMR (CDCl$_3$) δ=1.80 (5H, m), 2.00 (3H, s), 2.11 (2H, m), 2.60 (3H, d, J=2.9 Hz), 3.26 (1H, m), 3.73 (1H, d, J=12.7 Hz), 3.74 (3H, s), 3.79 (1H, d, J=12.7 Hz), 5.13 (1H, m), 7.27 (1H, m), 8.27 (1H, s)

ESI-MS (+20 eV) m/z 321.2 [M+H]$^+$

Example 4

1-Ethyl-3-[(1S,3R)-3-fluorocyclopentylamino]methyl-5-(5-fluoro-6-methylpyridin-3-yl)-4-methyl-1H-pyrazole According to the reaction step of Example 1 but using the compound obtained in Production Example 18 in place of the compound obtained in Production Example 15, the entitled compound was obtained.

$^1$H-NMR (CDCl$_3$) δ=1.32 (3H, t, J=7.2 Hz), 1.77 (5H, m), 1.97 (3H, s), 2.12 (2H, m), 2.60 (3H, d, J=2.7 Hz), 3.26 (1H, m), 3.76 (1H, d, J=13.1 Hz), 3.80 (1H, d, J=13.1 Hz), 4.01 (2H, q, J=7.2 Hz), 5.13 (1H, m), 7.27 (1H, m), 8.26 (1H, s)
ESI-MS (+20 eV) m/z 335.2 [M+H]$^+$

Example 5

3-[(1S,3R)-3-fluorocyclopentylamino]methyl-5-(5-fluoro-6-methylpyridin-3-yl)-4-methyl-1-propyl-1H-pyrazole According to the reaction step of Example 1 but using the compound obtained in Production Example 19 in place of the compound obtained in Production Example 15, the entitled compound was obtained.
$^1$H-NMR (CDCl$_3$) δ=0.79 (3H, t, J=7.4 Hz), 1.78 (7H, m), 1.97 (3H, s), 2.11 (2H, m), 2.60 (3H, d, J=2.7 Hz), 3.25 (1H, m), 3.76 (1H, d, J=13.0 Hz), 3.80 (1H, d, J=13.0 Hz), 3.91 (2H, m), 5.13 (1H, m), 7.27 (1H, m), 8.26 (1H, s)
ESI-MS (+20 eV) m/z 349.2 [M+H]$^+$ Example 6

1-Cyclopropyl-3-[(1S,3R)-3-fluorocyclopentylamino]methyl-5-(5-fluoro-6-methylpyridin-3-yl)-4-methyl-1H-pyrazole According to the reaction step of Example 1 but using the compound obtained in Production Example 20 in place of the compound obtained in Production Example 15, the entitled compound was obtained.
$^1$H-NMR (CDCl$_3$) δ=0.86 (2H, m), 1.00 (2H, m), 1.79 (5H, m), 2.01 (3H, s), 2.18 (2H, m), 2.60 (3H, d, J=2.7 Hz), 3.25 (1H, m), 3.39 (1H, m), 3.73 (1H, d, J=13.0 Hz), 3.76 (1H, d, J=13.0 Hz), 5.13 (1H, m), 7.38 (1H, m), 8.36 (1H, s)
ESI-MS (+20 eV) m/z 347.1 [M+H]$^+$ Example 7

3-[(1S,3R)-3-fluorocyclopentylamino]methyl-5-(5-fluoro-6-methylpyridin-3-yl)-4-methyl-1H-pyrazole 1) 1-Benzyl-3-[(1S,3R)-3-fluorocyclopentylamino]methyl-5-(5-fluoro-6-methylpyridin-3-yl)-4-methyl-1H-pyrazole According to the reaction step of Example 1 but using the compound obtained in Production Example 21 in place of the compound obtained in Production Example 15, the entitled compound was obtained.

2) 3-[(1S,3R)-3-fluorocyclopentylamino]methyl-5-(5-fluoro-6-methylpyridin-3-yl)-4-methyl-1H-pyrazole The compound (45 mg) obtained in 1) was dissolved in methanol (5 ml), and active carbon-held palladium (25 mg) and 1 N hydrogen chloride/methanol (1 ml) were added, and stirred overnight under 1-atmospheric pressure (101.3 KPa) of a hydrogen at room temperature. The insoluble matter was removed by filtration through Celite, and the filtrate was concentrated. The residue was purified by silica gel preparative thin-layer chromatography (chloroform/methanol=10/1) to obtain the entitled compound (4 mg) as a colorless oil.

$^1$H-NMR (CDCl$_3$) δ=1.95 (8H, m), 2.17 (3H, s), 2.56 (3H, d, J=2.9 Hz), 3.27 (1H, m), 3.87 (2H, s), 5.16 (1H, m), 7.64 (1H, d, J=10.4 Hz), 8.59 (1H, s)
ESI-MS (+20 eV) m/z 307.2 [M+H]$^+$

Example 8

5-(3,5-Difluorophenyl)-3-[(1S,3R)-3-fluorocyclopentylamino]methyl-4-methyl-1H-pyrazole According to the reaction step of Example 1 but using the compound obtained in Production Example 22 in place of the compound obtained in Production Example 15, the entitled compound was obtained.
$^1$H-NMR (CDCl$_3$) δ=1.90 (8H, m), 2.18 (3H, s), 3.27 (1H, m), 3.85 (2H, m), 5.15 (1H, m), 6.76 (1H, m), 7.19 (2H, m)
ESI-MS (+20 eV) m/z 310.2 [M+H]$^+$ Example 9

5-(3,5-Difluorophenyl)-1,4-dimethyl-3-[(1S,3R)-3-fluorocyclopentylamino]methyl-1H-pyrazole According to the reaction step of Example 1 but using the compound obtained in Production Example 23 in place of the compound obtained in Production Example 15, the entitled compound was obtained.
$^1$H-NMR (CDCl$_3$) δ=1.74 (5H, m), 1.99 (3H, s), 2.01 (1H, m), 2.30 (1H, m), 3.26 (1H, m), 3.73 (3H, s), 3.76 (2H, m), 5.13 (1H, m), 6.88 (3H, m)
ESI-MS (+20 eV) m/z 324.2 [M+H]$^+$ Example 10

5-(3,5-Difluorophenyl)-4-ethyl-3-[(1S,3R)-3-fluorocyclopentylamino]methyl-1-methyl-1H-pyrazole According to the reaction step of Example 1 but using the compound obtained in Production Example 30 in place of the compound obtained in Production Example 15, the entitled compound was obtained.
$^1$H-NMR (CDCl$_3$) δ=1.03 (3H, t, J=7.3 Hz), 1.65-2.35 (6H, m), 2.40 (2H, q, J=7.3 Hz), 3.25-3.35 (1H, m), 3.69 (3H, s), 3.79 (2H, d, J=1.5 Hz), 5.02-5.24 (1H, m), 6.78-6.94 (3H, m)
ESI-MS (+20 eV) m/z 338.3 [M+H]$^+$ Example 11

5-(3,5-Difluorophenyl)-3-[(1S,3R)-3-fluorocyclopentylamino]methyl-4-isopropyl-1-methyl-1H-pyrazole According to the reaction step of Example 1 but using the compound obtained in Production Example 31 in place of the compound obtained in Production Example 15, the entitled compound was obtained.
$^1$H-NMR (CDCl$_3$) δ=1.14 (6H, d, J=6.8 Hz), 1.65-2.35 (6H, m), 2.72-2.88 (1H, m), 3.25-3.35 (1H, m), 3.61 (3H, s), 3.84 (2H, s), 5.02-5.24 (1H, m), 6.75-6.92 (3H, m)
ESI-MS (+20 eV) m/z 352.2 [M+H]$^+$

Example 12

4-Chloro-5-(3,5-difluorophenyl)-3-[(1S,3R)-3-fluorocyclopentylamino]methyl-1-methyl-1H-pyrazole According to the reaction step of Example 1 but using the compound obtained in Production Example 32 in place of the compound obtained in Production Example 15, the entitled compound was obtained.

$^1$H-NMR (CDCl$_3$) δ=1.60-2.30 (6H, m), 3.18-3.28 (1H, m), 3.76 (3H, s), 3.80 (2H, s), 5.00-5.20 (1H, m), 6.82-6.94 (3H, m)

ESI-MS (+20 eV) m/z 344.2 [M+H]$^+$

Example 13

1-(2-Cyanoethyl)-5-(3,5-difluorophenyl)-3-[(1S,3R)-3-fluorocyclopentylamino]methyl-4-methyl-1H-pyrazole According to the reaction step of Example 1 but using the compound obtained in Production Example 24 in place of the compound obtained in Production Example 15, the entitled compound was obtained.

$^1$H-NMR (CDCl$_3$) δ=1.79 (5H, m), 1.97 (3H, s), 2.11 (2H, m), 2.89 (2H, t, J=6.7 Hz), 3.26 (1H, m), 3.78 (2H, m), 4.21 (2H, t, J=6.7 Hz), 5.14 (1H, m), 6.90 (3H, m)

ESI-MS (+20 eV) m/z 363.2 [M+H]$^+$

Example 14

4-Ethyl-3-[(1S,3R)-3-fluorocyclopentylamino]methyl-1-methyl-5-(6-methylpyridin-3-yl)-1H-pyrazole According to the reaction step of Example 1 but using the compound obtained in Production Example 33 in place of the compound obtained in Production Example 15, the entitled compound was obtained.

$^1$H-NMR (CDCl$_3$) δ=1.03 (3H, t, J=7.8 Hz), 1.65-2.33 (6H, m), 2.38 (2H, q, J=7.8 Hz), 2.64 (3H, s), 3.23-3.34 (1H, m), 3.68 (3H, s), 3.80 (2H, d, J=1.5 Hz), 5.04-5.23 (1H, m), 7.28 (1H, d, J=7.3 Hz), 7.51 (1H, dd, J=2.4, 7.3 Hz), 8.45 (1H, d, J=2.4 Hz)

ESI-MS (+20 eV) m/z 317.3 [M+H]$^+$

Example 15

5-(3,5-Difluorophenyl)-3-[(1S,3R)-3-fluorocyclopentylamino]methyl-4-methoxymethyl-1-methyl-1H-pyrazole 1) 5-(3,5-Difluorophenyl)-3-[(1S,3R)-3-fluorocyclopentylamino]methyl-1-methyl-4-vinyl-1H-pyrazole According to the reaction step of Example 1 but using the compound obtained in Production Example 34 in place of the compound obtained in Production Example 15, the entitled compound was obtained.

2) 3-({(tert-butoxycarbonyl)[(1S,3R)-3-fluorocyclopentyl]amino}methyl)-5-(3,5-difluorophenyl)-1-methyl-4-vinyl-1H-pyrazole The compound obtained in 1) and di-tert-butyl dicarbonate (244 mg) were dissolved in chloroform (4 ml), and stirred at room temperature for 3 days. The reaction liquid was concentrated under reduced pressure, and the obtained residue was purified by silica gel column chromatography (hexane/ethyl acetate=4/1 to 1/1) to obtain the entitled compound (163 mg).

3) 3-({(tert-butoxycarbonyl)[(1S,3R)-3-fluorocyclopentyl]amino}methyl)-5-(3,5-difluorophenyl)-4-formyl-1-methyl-1H-pyrazole Aqueous 1% osmium tetraoxide solution (3 drops) was added to a tetrahydrofuran (3 ml)/water (3 ml) suspension of the compound (146 mg) obtained in 2) and sodium periodate (215 mg), and stirred at room temperature for 2 hours. Aqueous 10% sodium sulfite solution was added to the reaction liquid, and extracted with ethyl acetate. The extract was washed with saturated saline water, dried with anhydrous magnesium sulfate, then the solvent was evaporated off, and the residue was purified by silica gel column chromatography (hexane/ethyl acetate=4/1 to 1/1) to obtain the entitled compound (98 mg).

4) 3-({(tert-butoxycarbonyl)[(1S,3R)-3-fluorocyclopentyl]amino}methyl)-5-(3,5-difluorophenyl)-4-hydroxymethyl-1-methyl-1H-pyrazole Sodium borohydride (10 mg) was added to a methanol (2 ml) solution of the compound (98 mg) obtained in 3), and stirred at room temperature for 30 minutes. Water was added to the reaction liquid, and extracted with ethyl acetate. The extract was washed with saturated saline water, dried with anhydrous magnesium sulfate, and the solvent was evaporated off to obtain the entitled compound as a crude product.

5) 3-({(tert-butoxycarbonyl)[(1S,3R)-3-fluorocyclopentyl]amino}methyl)-5-(3,5-difluorophenyl)-4-methoxymethyl-1-methyl-1H-pyrazole At 0° C., 60% sodium hydride (oil dispersion) (4 mg) was added to a tetrahydrofuran (1 ml) solution of the compound obtained in 4), and stirred at the same temperature for 10 minutes. At 0° C., methyl iodide (12 μl) was added to the reaction liquid, and stirred overnight at room temperature. Water was added to the reaction liquid, and extracted with ethyl acetate. The extract was washed with saturated saline water, then dried with anhydrous magnesium sulfate, and the solvent was evaporated off to obtain a crude product of the entitled compound.

6) 5-(3,5-Difluorophenyl)-3-[(1S,3R)-3-fluorocyclopentylamino]methyl-4-methoxymethyl-1-methyl-1H-pyrazole The compound obtained in 5) was dissolved in methanol (0.5 ml) and 4 N hydrogen chloride/dioxane solution (0.5 ml), and stirred at room temperature for 2 hours. The reaction liquid was concentrated under reduced pressure, and the obtained residue was purified by silica gel preparative thin-layer chromatography (chloroform/methanol/aqueous ammonia=150/10/1) to obtain the entitled compound (15 mg) as a colorless oil.

$^1$H-NMR (CDCl$_3$) δ=1.60-2.30 (6H, m), 3.22-3.35 (1H, m), 3.33 (3H, s), 3.77 (3H, s), 3.86 (2H, s), 4.20 (2H, s), 5.02-5.25 (1H, m), 6.85-6.96 (3H, m)

ESI-MS (+20 eV) m/z 354.2 [M+H]$^+$

Example 16

1-(3,5-Difluorophenyl)-5-ethyl-2-methyl-4-[(1S,3R)-3-fluorocyclopentylamino]methyl-1H-imidazole According to the reaction step of Example 1 but using the compound obtained in Production Example 38 in place of the compound obtained in Production Example 15, the entitled compound was obtained.

$^1$H-NMR (CDCl$_3$) δ=0.91 (3H, t, J=7.6 Hz), 1.60-2.30 (7H, m), 2.19 (3H, s), 2.46 (2H, q, J=7.6 Hz), 3.24 (1H, m), 3.65 (2H, d, J=1.9 Hz), 5.10 (1H, m), 6.78 (2H, m), 6.96 (1H, m)
ESI-MS (+20 eV) m/z 338.2 [M+H]$^+$

Example 17

3-[(1S,3R)-3-fluorocyclopentylamino]methyl-1-methyl-4-methoxymethyl-5-(6-methylpyridin-3-yl)-1H-pyrazole According to the reaction step of Example 1 but using the compound obtained in Production Example 35 in place of the compound obtained in Production Example 15, the entitled compound was obtained.

$^1$H-NMR (CDCl$_3$) δ=1.64-2.31 (6H, m), 2.64 (3H, s), 3.20-3.34 (1H, m), 3.31 (3H, s), 3.75 (3H, s), 3.87 (2H, s), 4.19 (2H, s), 5.02-5.22 (1H, m), 7.29 (1H, d, J=7.8 Hz), 7.60 (1H, dd, J=2.4, 7.8 Hz), 8.51 (1H, d, J=2.4 Hz)
ESI-MS (+20 eV) m/z 333.3 [M+H]$^+$

Example 18

5-(3,5-Difluorophenyl)-1-ethyl-3-[(1S,3R)-3-fluorocyclopentylamino]methyl-4-methyl-1H-pyrazole According to the reaction step of Example 1 but using the compound obtained in Production Example 25 in place of the compound obtained in Production Example 15, the entitled compound was obtained.

$^1$H-NMR (CDCl$_3$) δ=1.31 (3H, t, J=7.2 Hz), 1.80 (4H, m), 1.97 (3H, s), 2.16 (2H, m), 3.25 (1H, m), 3.75 (1H, d, J=13.0 Hz), 3.79 (1H, d, J=13.0 Hz), 4.02 (2H, q, J=7.2 Hz), 5.13 (1H, m), 6.85 (3H, m)
ESI-MS (+20 eV) m/z 338.3 [M+H]$^+$

Example 19

5-(3,5-Difluorophenyl)-3-[(1S,3R)-3-fluorocyclopentylamino]methyl-4-methoxymethyl-1H-pyrazole 1) 5-(3,5-Difluorophenyl)-3-[(1S,3R)-3-fluorocyclopentylamino]methyl-4-methoxymethyl-1-{[2-(trimethylsilyl)ethoxy]methyl}-1H-pyrazole According to the reaction step of Example 1 but using the compound obtained in Production Example 36 in place of the compound obtained in Production Example 15, the entitled compound was obtained.

2) 5-(3,5-Difluorophenyl)-3-[(1S,3R)-3-fluorocyclopentylamino]methyl-4-methoxymethyl-1H-pyrazole The compound obtained in 1) was dissolved in trifluoroacetic acid (11.7 ml) and water (1.3 ml), and stirred at room temperature for 3 hours. Water was added to the reaction liquid, neutralized with sodium hydrogencarbonate, and extracted with ethyl acetate. The extract was washed with saturated saline water, dried with anhydrous magnesium sulfate, then the solvent was evaporated off, and the obtained residue was purified by silica gel column chromatography (chloroform/methanol=50/1 to 30/1 to 20/1) to obtain the entitled compound (928 mg) as a white solid.

$^1$H-NMR (CDCl$_3$) δ=1.65-2.20 (6H, m), 3.22-3.31 (1H, m), 3.42 (3H, s), 3.95 (2H, d, J=1.4 Hz), 4.34 (2H, s), 5.06-5.25 (1H, m), 6.74-6.82 (1H, m), 7.22-7.31 (2H, m)
ESI-MS (+20 eV) m/z 340.3 [M+H]$^+$

Example 20

5-(3,5-Difluorophenyl)-1,4-dimethyl-3-[(1S,3R)-3-hydroxycyclopentylamino]methyl-1H-pyrazole According to the reaction step of Example 1 but using the compound obtained in Production Example 23 in place of the compound obtained in Production Example 15 and using (1S,3R)-3-hydroxycyclopentylamine (this was provisionally referred to as 1S,3R since the absolute configuration was unidentified) in place of the compound obtained in Production Example 43, the entitled compound was obtained.

$^1$H-NMR (CDCl$_3$) δ=1.59-1.65 (1H, m), 1.73-1.95 (5H, m), 1.98 (3H, s), 3.44 (1H, brs), 3.73 (1H, d, J=12.7 Hz), 3.74 (3H, s), 3.78 (1H, d, J=12.7 Hz), 4.27 (1H, brs), 6.80-6.91 (3H, m)
ESI-MS (+20 eV) m/z 322.3 [M+H]$^+$

Example 21

5-(3,5-Difluorophenyl)-1,4-dimethyl-3-(cis-4-fluorocyclohexylamino)methyl-1H-pyrazole According to the reaction step of Example 1 but using the compound obtained in Production Example 23 in place of the compound obtained in Production Example 15 and using the compound obtained in Production Example 45 in place of the compound obtained in Production Example 43, the entitled compound was obtained.

$^1$H-NMR (CDCl$_3$) δ=1.48-1.66 (4H, m), 1.78-1.83 (2H, m), 1.99 (3H, s), 2.03-2.10 (2H, m), 2.61-2.67 (1H, m), 3.73 (3H, s), 3.80 (2H, s), 4.69-4.83 (1H, m), 6.80-6.90 (3H, m)
ESI-MS (+20 eV) m/z 338.3 [M+H]$^+$

Example 22

5-(3,5-Difluorophenyl)-1,4-dimethyl-3-(cis-4-methoxycyclohexylamino)methyl-1H-pyrazole According to the reaction step of Example 1 but using the compound obtained in Production Example 23 in place of the compound obtained in Production Example 15 and using cis-4-methoxycyclohexylamine in place of the compound obtained in Production Example 43, the entitled compound was obtained.

$^1$H-NMR (CDCl$_3$) δ=1.46-1.62 (4H, m), 1.67-1.73 (2H, m), 1.87-1.90 (2H, m), 1.99 (3H, s), 2.61-2.67 (1H, m), 3.31 (3H, s), 3.34-3.38 (1H, m), 3.73 (3H, s), 3.78 (2H, s), 6.80-6.90 (3H, m)
ESI-MS (+20 eV) m/z 350.3 [M+H]$^+$

Example 23

5-(3,5-Difluorophenyl)-3-[(1S,2R)-2-fluorocyclopentylamino]methyl-4-methoxymethyl-1H-pyrazole According to the reaction step of Example 19 but using the compound obtained in Production Example 44 in place of the compound obtained in Production Example 43, the entitled compound was obtained.

$^1$H-NMR (CDCl$_3$) δ=1.48-1.65 (2H, m), 1.78-2.10 (4H, m), 2.92-3.09 (1H, m), 3.33 (3H, s), 4.00 (1H, d, J=14.6 Hz), 4.07 (1H, d, J=14.6 Hz), 4.34 (2H, d, J=1.0 Hz), 4.93-5.12 (1H, m), 6.75-6.82 (1H, m), 7.25-7.33 (2H, m)

ESI-MS (+20 eV) m/z 340.3 [M+H]$^+$

Example 24

5-(2,4-Dichlorophenyl)-1-(3,5-difluorophenyl)-2-methyl-4-[(1S,3R)-3-fluorocyclopentylamino]methyl-1H-pyrazole According to the reaction step of Example 1 but using the compound obtained in Production Example 40 in place of the compound obtained in Production Example 15, the entitled compound was obtained.

$^1$H-NMR (CDCl$_3$) δ=1.50-2.20 (6H, m), 2.35 (3H, s), 3.15 (1H, m), 3.50 (2H, dd, J=11.5, 13.1 Hz), 3.60 (2H, dd, J=6.1, 13.3 Hz), 5.07 (1H, m), 6.63 (2H, m), 6.80 (1H, m), 7.16 (2H, dd, J=3.1, 8.2 Hz), 7.22 (1H, dd, J=2.2, 8.2 Hz), 7.38 (1H, d, J=1.8 Hz)

ESI-MS (+20 eV) m/z 454.0 [M+H]$^+$, 456.1 [M−H]$^+$

Example 25

1-(3,5-Difluorophenyl)-2-ethyl-3-[(1S,3R)-3-fluorocyclopentylamino]methyl-5-methyl-1H-pyrrole According to the reaction step of Example 1 but using the compound obtained in Production Example 41 in place of the compound obtained in Production Example 15, the entitled compound was obtained.

$^1$H-NMR (CDCl$_3$) δ=0.89 (3H, t, J=7.6 Hz), 1.63-2.28 (9H, m), 2.46 (2H, q, J=7.5 Hz), 3.31-3.23 (1H, m), 3.62 (2H, s), 5.13 (1H, d, J=54.6 Hz), 5.96 (1H, s), 6.75-6.82 (2H, m), 6.89 (1H, tt, J=2.4, 8.9 Hz)

ESI-MS (+20 eV) m/z 337.3 [M+H]$^+$

Example 26

1-Cyclopropyl-5-(3,5-difluorophenyl)-3-[(1S,3R)-3-fluorocyclopentylamino]methyl-4-methyl-1H-pyrazole According to the reaction step of Example 1 but using the compound obtained in Production Example 26 in place of the compound obtained in Production Example 15, the entitled compound was obtained.

$^1$H-NMR (CDCl$_3$) δ=0.88 (2H, m), 0.99 (2H, m), 1.80 (5H, m), 2.00 (3H, s), 2.17 (2H, m), 3.24 (1H, m), 3.40 (1H, m), 3.72 (1H, d, J=13.1 Hz), 3.76 (1H, d, J=13.1 Hz), 5.13 (1H, m), 6.89 (3H, m)

ESI-MS (+20 eV) m/z 350.3 [M+H]$^+$

Example 27

5-(3,5-Difluorophenyl)-1-ethyl-4-methyl-3-(tetrahydro-2H-pyran-4-ylamino)methyl-1H-pyrazole According to the reaction step of Example 1 but using the compound obtained in Production Example 25 in place of the compound obtained in Production Example 15 and using tetrahydro-2H-pyran-4-ylamine in place of the compound obtained in Production Example 43, the entitled compound was obtained.

$^1$H-NMR (CDCl$_3$) δ=1.31 (3H, t, J=7.2 Hz), 1.58 (3H, m), 1.91 (2H, m), 1.97 (3H, s), 2.80 (1H, m), 3.44 (2H, m), 3.81 (2H, s), 4.01 (2H, m), 4.02 (2H, q, J=7.2 Hz), 6.85 (3H, m)

ESI-MS (+20 eV) m/z 336.2 [M+H]$^+$

Example 28

5-(3,5-Difluorophenyl)-4-methyl-3-(cis-4-fluorocyclohexylamino)methyl-1H-pyrazole According to the reaction step of Example 1 but using the compound obtained in Production Example 22 in place of the compound obtained in Production Example 15 and using the compound obtained in Production Example 45 in place of the compound obtained in Production Example 43, the entitled compound was obtained.

$^1$H-NMR (CDCl$_3$) δ=1.45-1.62 (4H, m), 1.78-1.81 (2H, m), 2.05-2.06 (2H, m), 2.17 (3H, s), 2.55-2.61 (1H, m), 3.89 (3H, s), 4.71-4.85 (2H, m), 6.74-6.80 (1H, m), 7.15-7.21 (2H, m)

ESI-MS (+20 eV) m/z 324.2 [M+H]$^+$

Example 29

1-(3,5-Difluorophenyl-5-ethyl-4-(cis-4-fluorocyclohexylamino(methyl-2-methyl-1H-imidazole According to the reaction step of Example 1 but using the compound obtained in Production Example 38 in place of the compound obtained in Production Example 15 and using the compound obtained in Production Example 45 in place of the compound obtained in Production Example 43, the entitled compound was obtained.

$^1$H-NMR (CDCl$_3$) δ=0.92 (3H, t, J=7.6 Hz), 1.60 (2H, m), 1.80 (2H, m), 2.06 (4H, m), 2.20 (3H, s), 2.46 (2H, q, J=7.6 Hz), 2.63 (1H, m), 3.68 (2H, s), 4.78 (1H, m), 6.80 (2H, m), 6.98 (1H, m)

ESI-MS (+20 eV) m/z 352.2 [M+H]$^+$

Example 30

5-(3,5-Difluorophenyl)-3-(cyclopentylamino)methyl-4-methoxymethyl-1H-pyrazole According to the reaction step of Example 19 but using cyclopentylamine in place of the compound obtained in Production Example 43, the entitled compound was obtained.

$^1$H-NMR (CDCl$_3$) δ=1.35-1.94 (8H, m), 3.12-3.21 (1H, m), 3.42 (3H, s), 3.93 (2H, s), 4.34 (2H, s), 6.74-6.82 (1H, m), 7.22-7.32 (2H, m)

ESI-MS (+20 eV) m/z 322.3 [M+H]$^+$

Example 31

1-(3,5-Difluorophenyl)-5-isopropyl-2-methyl-4-[(1S,3R)-3-fluorocyclopentylamino]methyl-1H-imidazole According to the reaction step of Example 1 but using the compound obtained in Production Example 39 in place of the compound obtained in Production Example 15, the entitled compound was obtained.

¹H-NMR (CDCl₃) δ=1.18 (6H, d, J=7.3 Hz), 1.62-2.24 (6H, m), 2.13 (3H, s), 2.66 (1H, m), 3.22 (1H, m), 3.74 (2H, s), 5.14 (1H, m), 6.78 (2H, m), 6.98 (1H, m)
ESI-MS (+20 eV) m/z 352.2 [M+H]⁺

Example 32

1,4-Dimethyl-3-(cis-4-fluorocyclohexylamino)methyl-5-(3,4,5-trifluorophenyl)-1H-pyrazole According to the reaction step of Example 1 but using the compound obtained in Production Example 29 in place of the compound obtained in Production Example 15 and using the compound obtained in Production Example 45 in place of the compound obtained in Production Example 43, the entitled compound was obtained.
¹H-NMR (CDCl₃) δ=1.47-1.66 (4H, m), 1.78-1.82 (2H, m), 1.97 (3H, s), 2.02-2.10 (2H, m), 2.61-2.68 (1H, m), 3.72 (3H, s), 3.79 (2H, s), 4.70-4.84 (1H, m), 6.89-6.97 (2H, m)
ESI-MS (+20 eV) m/z 356.2 [M+H]⁺

Example 33

1-(3,5-Difluorophenyl)-3-[(1S,3R)-3-fluorocyclopentylamino]methyl-2-methoxymethyl-5-methyl-1H-pyrrole tartrate 1) 1-(3,5-Difluorophenyl)-3-[(1S,3R)-3-fluorocyclopentylamino]methyl-2-methoxymethyl-5-methyl-1H-pyrrole According to the reaction step of Example 1 but using the compound obtained in Production Example 42 in place of the compound obtained in Production Example 15, the entitled compound was obtained.

2) 1-(3,5-Difluorophenyl)-3-[(1S,3R)-3-fluorocyclopentylamino]methyl-2-methoxymethyl-5-methyl-1H-pyrrole tartrate The compound (15 mg) obtained in 1) and L-tartaric acid (6.5 mg) were dissolved in methanol (1 ml), and the solvent was evaporated off to obtain the entitled compound (21 mg) as a white solid.
¹H-NMR (CD₃OD) δ=1.63-2.45 (9H, m), 3.14 (3H, s), 3.60-3.68 (1H, m), 4.05 (2H, d, J=2.4 Hz), 4.12 (2H, s), 4.30 (2H, s), 5.10 (1H, d, J=53.4 Hz), 6.08 (1H, s), 6.87-6.95 (2H, m), 7.05-7.12 (1H, m)
ESI-MS (+20 eV) m/z 353.1 [M+H]⁺

Example 34

5-(3,5-Difluorophenyl)-3-(cis-4-methoxycyclohexylamino)methyl-4-methoxymethyl-1H-pyrazole According to the reaction step of Example 19 but using cis-4-methoxycyclohexylamine in place of the compound obtained in Production Example 43, the entitled compound was obtained.
¹H-NMR (CDCl₃) δ=1.40-1.60 (4H, m), 1.65-1.74 (2H, m), 1.82-1.92 (2H, m), 2.55-2.65 (1H, m), 3.31 (3H, s), 3.32-3.45 (1H, m), 3.41 (3H, s), 3.98 (2H, s), 4.34 (2H, s), 6.74-6.82 (1H, m), 7.22-7.32 (2H, m)
ESI-MS (+20 eV) m/z 366.3 [M+H]⁺

Example 35

5-(3,5-Difluorophenyl)-1-isopropyl-4-methyl-3-(tetrahydro-2H-pyran-4-ylamino)methyl-1H-pyrazole According to the reaction step of Example 1 but using the compound obtained in Production Example 27 in place of the compound obtained in Production Example 15 and using tetrahydro-2H-pyran-4-ylamine in place of the compound obtained in Production Example 43, the entitled compound was obtained.
¹H-NMR (CDCl₃) δ=1.41 (6H, d, J=6.7 Hz), 1.51 (2H, m), 1.69 (1H, m), 1.90 (2H, m), 1.95 (3H, s), 2.80 (1H, m), 3.43 (2H, m), 3.81 (2H, s), 4.00 (2H, m), 4.32 (1H, m), 6.84 (3H, m)
ESI-MS (+20 eV) m/z 350.3 [M+H]⁺

Example 36

3-[(1S,3R)-3-fluorocyclopentylamino]methyl-4-methoxymethyl-5-(3,4,5-trifluorophenyl)-1H-pyrazole According to the reaction step of Example 19 but using the compound obtained in Production Example 37 in place of the compound obtained in Production Example 36, the entitled compound was obtained.
¹H-NMR (CDCl₃) δ=1.68-2.17 (6H, m), 3.23-3.29 (1H, m), 3.42 (3H, s), 3.92 (1H, d, J=14.9 Hz), 3.96 (1H, d, J=14.9 Hz), 4.31 (2H, s), 5.08-5.24 (1H, m), 7.39-7.46 (2H, m)
ESI-MS (+20 eV) m/z 358.1 [M+H]⁺, 356.1 [M−H]⁺

Example 37

5-(4-Chloro-3,5-difluorophenyl)-1-ethyl-3-[(1S,3R)-3-fluorocyclopentylamino]methyl-4-methyl-1H-pyrazole According to the reaction step of Example 1 but using the compound obtained in Production Example 28 in place of the compound obtained in Production Example 15, the entitled compound was obtained.
¹H-NMR (CDCl₃) δ=1.31 (3H, t, J=7.3 Hz), 1.80 (5H, m), 1.97 (3H, s), 2.16 (2H, m), 3.25 (1H, m), 3.75 (1H, d, J=13.1 Hz), 3.79 (1H, d, J=13.1 Hz), 4.01 (2H, q, J=7.3 Hz), 5.13 (1H, m), 6.93 (2H, m)
ESI-MS (+20 eV) m/z 372.2 [M+H]⁺

Example 38

1-(3,5-Difluorophenyl)-4-(cis-4-fluorocyclohexylamino)methyl-5-ethyl-2-methyl-1H-imidazole According to the reaction step of Example 1 but using the compound obtained in Production Example 38 in place of the compound obtained in Production Example 15 and using the compound obtained in Production Example 45 in place of the compound obtained in Production Example 43, the entitled compound was obtained.
¹H-NMR (CDCl₃) δ=0.92 (3H, t, J=7.6 Hz), 1.60 (2H, m), 1.80 (2H, m), 2.06 (4H, m), 2.20 (3H, s), 2.46 (2H, q, J=7.6 Hz), 2.63 (1H, m), 3.68 (2H, s), 4.78 (1H, m), 6.80 (2H, m), 6.98 (1H, m)
ESI-MS (+20 eV) m/z 352.2 [M+H]⁺

Example 39

5-(3,5-Difluorophenyl)-4-methoxymethyl-3-(tetrahydro-2H-pyran-4-ylamino)methyl-1H-pyrazole According to the reaction step of Example 19 but using tetrahydro-2H-pyran-4-ylamine in place of the compound obtained in Production Example 43, the entitled compound was obtained as a colorless oil.

$^1$H-NMR (CDCl$_3$) δ=1.39-1.51 (2H, m), 1.83-1.92 (2H, m), 2.72-2.82 (1H, m), 3.35-3.43 (5H, m), 3.94-4.02 (4H, m), 4.34 (2H, s), 6.76-6.84 (1H, m), 7.21-7.28 (2H, m)

ESI-MS (+20 eV) m/z 338.3 [M+H]$^+$

Example 40

5-(3,5-Difluorophenyl)-4-methoxymethyl-1-methyl-3-(tetrahydro-2H-pyran-4-ylamino)methyl-1H-pyrazole

1) 3-{(Tert-butoxycarbonyl)(tetrahydro-2H-pyran-4-yl)amino}methyl-5-(3,5-difluorophenyl)-4-methoxymethyl-1H-pyrazole The compound (36 mg) obtained in Example 39 and di-tert-butyl dicarbonate (28 mg) were dissolved in chloroform (2 ml), and stirred overnight at room temperature. The reaction liquid was concentrated under reduced pressure, and the obtained residue was purified by silica gel column chromatography (hexane/ethyl acetate 4/1 to 1/1) to obtain the entitled compound (40 mg).

2) 3-{(Tert-butoxycarbonyl)(tetrahydro-2H-pyran-4-yl)amino}methyl-5-(3,5-difluorophenyl)-4-methoxymethyl-1-methyl-1H-pyrazole At 0° C., 60% sodium hydride (oil dispersion) (12 mg) was added to a tetrahydrofuran (1 ml) solution of the compound obtained in 1), and stirred at the same temperature for 10 minutes. At 0° C., methyl iodide (30 μl) was added to the reaction liquid, and stirred overnight at room temperature. Water was added to the reaction liquid, and extracted with ethyl acetate. The extract is washed with saturated saline water, dried with anhydrous magnesium sulfate, then the solvent was evaporated off, and the obtained residue was purified by silica gel column chromatography (hexane/ethyl acetate=9/1 to 1/1) to obtain the entitled compound (29 mg).

3) 5-(3,5-Difluorophenyl)-4-methoxymethyl-1-methyl-3-(tetrahydro-2H-pyran-4-ylamino)methyl-1H-pyrazole The compound obtained in 2) was dissolved in trifluoroacetic acid (0.5 ml), and stirred at room temperature for 1 hour. The reaction liquid was concentrated, then the obtained residue was purified by preparative thin-layer chromatography (chloroform/methanol/aqueous ammonia=100/10/1) to obtain the entitled compound (20 mg) as a colorless oil.

$^1$H-NMR (CDCl$_3$) δ=1.45-1.56 (2H, m), 1.86-2.03 (2H, m), 2.76-2.84 (1H, m), 3.32 (5H, s), 3.37-3.48 (2H, m), 3.77 (3H, s), 3.88 (2H, s), 3.96-4.03 (2H, m), 4.19 (2H, s), 6.88-6.95 (3H, m)

ESI-MS (+20 eV) m/z 352.3 [M+H]$^+$

Example 41

5-(4-Chloro-3,5-difluorophenyl)-3-[(1S,3R)-3-fluorocyclopentylamino]methyl-4-methoxymethyl-1-methyl-1H-pyrazole According to the reaction step of Example 1 but using the compound obtained in Production Example 46 in place of the compound obtained in Production Example 15, the entitled compound was obtained.

$^1$H-NMR (CDCl$_3$) δ=1.90 (5H, m), 2.01 (2H, m), 2.20 (1H, m), 3.25 (1H, m), 3.33 (3H, s), 3.78 (3H, s), 3.83 (2H, s), 4.18 (2H, s), 5.19 (1H, m), 7.06 (2H, m)

ESI-MS (+20 eV) m/z 388.2 [M+H]$^+$

INDUSTRIAL APPLICABILITY

The compounds exhibit an antagonism to binding of nociceptin to a nociceptin receptor ORL1 (opioid receptor-like-1 receptor) and are useful as an analgesic against diseases accompanied with pains such as cancerous pain, postoperative pain, migraine, gout, chronic rheumatism, chronic pain and neuralgia; a reliever against tolerance to narcotic analgesics such as morphine; a reliever against dependence on or addiction to narcotic analgesics such as morphine; an analgesic enhancer; an antiobesitic or appetite suppressor; a treating or prophylactic agent for learning and memory impairment or dementia in aging, cerebrovascular diseases and Alzheimer's disease; an agent for treating developmental cognitive abnormality such as attention deficit hyperactivity disorder and learning disability; a remedy for schizophrenia; an agent for treating neurodegenerative diseases such as Parkinsonism and chorea; an anti-depressant or treating agent for affective disorders; a treating or prophylactic agent for diabetes insipidus; a treating or prophylactic agent for polyuria; a remedy for hypotension.

The invention claimed is:

1. A compound of the formula (I):

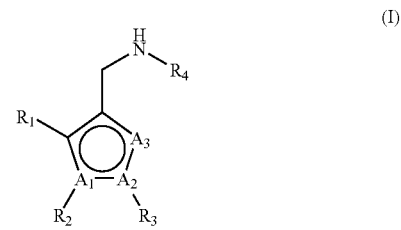

wherein:
A$_1$, A$_2$ and A$_3$ are the same or different, each representing a carbon atom or a nitrogen atom, provided that at least one of A$_1$, A$_2$ and A$_3$ is a carbon atom, and at least one of A$_1$, A$_2$ and A$_3$ is a nitrogen atom;

R$^1$ represents a halogen atom, a C$_{1-6}$ alkyl group which is unsubstituted or substituted with a C$_{1-6}$ alkoxy group, or a phenyl group substituted with a halogen atom;

R$^2$ represents a phenyl group which is unsubstituted or substituted with a halogen atom or a C$_{1-6}$ alkyl group; a pyridinyl group which is unsubstituted or substituted with a halogen atom or a C$_{1-6}$ alkyl group; or a thiazolyl group which is unsubstituted or substituted with a halogen atom or a C$_{1-6}$ alkyl group;

R$^3$ represents a hydrogen atom; a C$_{1-6}$ alkyl group which is unsubstituted or substituted with a hydroxyl group, a halogen atom, a C$_{1-6}$ alkoxy group or a cyano group; or a $C_{3-6}$ cycloalkyl group which is unsubstituted or substituted with a hydroxyl group or a halogen atom;

$R^4$ represents a $C_{1-6}$ alkyl group; a $C_{3-6}$ cycloalkyl group which is unsubstituted or substituted with a halogen atom, a hydroxyl group or a $C_{1-6}$ alkoxy group; a $C_{3-6}$ cycloalkyl-$C_{1-6}$ alkyl group which is unsubstituted or substituted with a halogen atom, a hydroxyl group or a $C_{1-6}$ alkoxy group; or a tetrahydro-2H-pyran-4-yl group;

or a pharmaceutically acceptable salt thereof.

2. The compound of claim 1 wherein only one of $A_1$, $A_2$ and $A_3$ is a carbon atom and the other two of $A_1$, $A_2$ and $A_3$ are nitrogen atoms.

3. The compound of claim 1 of the formula (I-a):

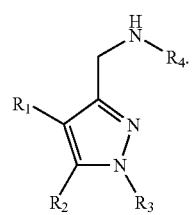

(I-a)

4. The compound of claim 1 of the formula (I-b):

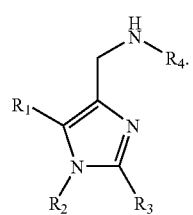

(I-b)

5. The compound of claim 1 of the formula (I-c):

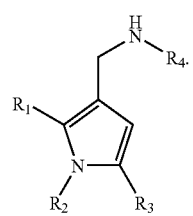

(I-c)

6. The compound of claim 1 wherein $R^1$ is a methyl group, an ethyl group, an isopropyl group or a methoxyethyl group.

7. The compound of claim 1 wherein $R^2$ is a 4-fluorophenyl group, a 3,5-difluorophenyl group, a 3,4,5-trifluorophenyl group, a 4-chloro-3,5-difluorophenyl group, a 2-methylpyridin-5-yl group, a 3-fluoro-2-methylpyridin-5-yl group or a 2-methyl-1,3-thiazol-5-yl group.

8. The compound of claim 1 wherein $R^3$ is a hydrogen atom, a methyl group, a 2-cyanoethyl group, a tert-butyl group or a cyclopropyl group.

9. The compound of claim 1 wherein $R^4$ is a 3-fluorocyclopentyl group, a 3-hydroxycyclopentyl group, a 4-methoxycyclohexyl group or a 4-fluorocyclohexyl group.

10. A compound which is selected from the group consisting of:
- 3-[(1S,3R)-3-fluorocyclopentylamino]methyl-5-(5-fluoro-6-methylpyridin-3-yl)-1-isopropyl-4-methyl-1H-pyrazole;
- 5-(3,5-difluorophenyl-3-[(1S,3R)-3-fluorocyclopentylamino]methyl-4-methyl-1H-pyrazole;
- 1-(2-cyanoethyl)-5-(3,5-difluorophenyl)-3-[(1S,3R)-3-fluorocyclopentylamino]methyl-4-methyl-1H-pyrazole;
- 5-(3,5-difluorophenyl)-3-[(1S,3R)-3-fluorocyclopentylamino]methyl-4-methoxymethyl-1-methyl-1H-pyrazole;
- 1-(3,5-difluorophenyl)-5-ethyl-2-methyl-4-[(1S,3R)-3-fluorocyclopentylamino]methyl-1H-imidazole;
- 5-(3,5-difluorophenyl)-3-[(1S,3R)-3-fluorocyclopentylamino]methyl-4-methoxymethyl-1H-pyrazole;
- 5-(3,5-difluorophenyl)-3-[(1S,2R)-2-fluorocyclopentylamino]methyl-4-methoxymethyl-1H-pyrazole;
- 1-cyclopropyl-5-(3,5-difluorophenyl)-3-[(1S,3R)-3-fluorocyclopentylamino]methyl-4-methyl-1H-pyrazole;
- 5-(3,5-difluorophenyl)-3-(cyclopentylamino)methyl-4-methoxymethyl-1H-pyrazole;
- 3-[(1S,3R)-3-fluorocyclopentylamino]methyl-4-methoxymethyl-5-(3,4,5-trifluorophenyl)-1H-pyrazole;
- 5-(4-chloro-3,5-difluorophenyl)-1-ethyl-3-[(1S,3R)-3-fluorocyclopentylamino]methyl-4-methyl-1H-pyrazole; and
- 1-(3,5-difluorophenyl)-4-(cis-4-fluorocyclohexylamino)methyl-5-ethyl-2-methyl-1H-imidazole;

or a pharmaceutically acceptable salt thereof.

11. The compound of claim 10 which is 3-[(1S,3R)-3-fluorocyclopentylamino]methyl-5-(5-fluoro-6-methylpyridin-3-yl)-1-isopropyl-4-methyl-1H-pyrazole, or a pharmaceutically acceptable salt thereof.

12. The compound of claim 10 which is 5-(3,5-difluorophenyl-3-[(1S,3R)-3-fluorocyclopentylamino]methyl-4-methyl-1H-pyrazole, or a pharmaceutically acceptable salt thereof.

13. The compound of claim 10 which is 1-(2-cyanoethyl)-5-(3,5-difluorophenyl)-3-[(1S,3R)-3-fluorocyclopentylamino]methyl-4-methyl-1H-pyrazole, or a pharmaceutically acceptable salt thereof.

14. The compound of claim 10 which is 1-(3,5-difluorophenyl)-5-ethyl-2-methyl-4-[1S,3R)-3-fluorocyclopentylamino]methyl-1H-imidazole, or a pharmaceutically acceptable salt thereof.

15. The compound of claim 10 which is 5-(3,5-difluorophenyl)-3-[(1S,3R)-3-fluorocyclopentylamino]methyl-4-methoxymethyl-1H-pyrazole, or a pharmaceutically acceptable salt thereof.

16. The compound of claim 10 which is 1-(3,5-difluorophenyl)-4-(cis-4-fluorocyclohexylamino)methyl-5-ethyl-2-methyl-1H-imidazole, or a pharmaceutically acceptable salt thereof.

17. A pharmaceutical composition comprising a pharmaceutically acceptable adjuvant and the compound of claim 1 or a pharmaceutically acceptable salt thereof.

18. A pharmaceutical composition comprising a pharmaceutically acceptable adjuvant and the compound of claim 10 or a pharmaceutically acceptable salt thereof.

* * * * *